(12) United States Patent
Ebden et al.

(10) Patent No.: US 7,482,355 B2
(45) Date of Patent: Jan. 27, 2009

(54) PYRIMIDINE DERIVATIVES AS MODULATORS OF CHEMOKINE RECEPTOR ACTIVITY

(75) Inventors: Mark Richard Ebden, Loughborough (GB); Premji Meghani, Loughborough (GB); Anthony Ronald Cook, Loughborough (GB); John Steele, Loughborough (GB); Lal Lashkar Singh Cheema, Loughborough (GB)

(73) Assignee: AstraZeneca AB (SE)

( * ) Notice: Subject to any disclaimer, the term of this patent is extended or adjusted under 35 U.S.C. 154(b) by 341 days.

(21) Appl. No.: 10/525,495

(22) PCT Filed: Aug. 20, 2003

(86) PCT No.: PCT/GB03/03632

§ 371 (c)(1),
(2), (4) Date: Feb. 23, 2005

(87) PCT Pub. No.: WO2004/018435

PCT Pub. Date: Mar. 4, 2004

(65) Prior Publication Data

US 2006/0004030 A1    Jan. 5, 2006

(30) Foreign Application Priority Data

Aug. 24, 2002 (GB) .................................. 0219819.0
Oct. 8, 2002 (GB) .................................. 0223287.4

(51) Int. Cl.
   C07D 239/56        (2006.01)
   A61K 31/513        (2006.01)

(52) U.S. Cl. ....................................... 514/274; 544/301

(58) Field of Classification Search ................. 544/301; 514/274
   See application file for complete search history.

(56) References Cited

U.S. PATENT DOCUMENTS 3,673,184 A    6/1972   Minami et al.

FOREIGN PATENT DOCUMENTS

| GB | 1042295 | 9/1966 |
|---|---|---|
| JP | 61-118372 | 5/1986 |
| JP | 03-197467 | 8/1991 |
| WO | WO 91/15209 | 10/1991 |
| WO | WO 97/22596 | 6/1997 |
| WO | WO 97/30035 | 8/1997 |
| WO | WO 97/32856 | 9/1997 |
| WO | WO 98/13354 | 4/1998 |
| WO | WO 99/02166 | 1/1999 |
| WO | WO 99/41253 | 8/1999 |
| WO | WO 00/09511 | 2/2000 |
| WO | WO 00/40529 | 7/2000 |
| WO | WO 00/41669 | 7/2000 |
| WO | WO 00/76980 | 12/2000 |
| WO | WO 01/25242 | 4/2001 |
| WO | WO 01/58902 | 8/2001 |
| WO | WO 01/58906 | 8/2001 |
| WO | WO 01/92224 | 12/2001 |
| WO | WO 02/04434 | 1/2002 |
| WO | WO 02/08213 | 1/2002 |
| WO | WO 02/24665 | 3/2002 |
| WO | WO 02/064096 | 8/2002 |
| WO | WO 03/059893 A1 | 7/2003 |
| WO | WO 2004/011443 | 2/2004 |

OTHER PUBLICATIONS

Inoue et al., Caplus Abstract 115:280054 (1991).*
Inoue et al., Caplus Abstract 106:18604 (1987).*
Simone, Oncology: Introduction, Cecil Textbook of Medicine, 20th Edition, vol. 1, pp. 1004-1010, 1996.*
Bremner et al., Therapy of Crohn's Disease in childhood, Expert Opin Pharmacother. 3(7):809-825, 2002.*
Robinson, Medican Therapy of Inflammatory Bowel Disease for the 21st Century, Eur J Surg Suppl 582, pp. 90-98, 1998.*
Singh et al., Immune therapy in inflammatory bowel disease and models of colitis, British Journal of Surgery, 88, pp. 1558-1569, 2001.*
Havlioglu et al., Slit proteins, potential endogenous modulators of inflammation, Journal of NeuroVirology, 8, pp. 486-495, 2002.*
Vippagunta et al., Crystalline Solids, Advanced Drug Delivery Reviews, 48, pp. 3-26, 2001.*
West, Solid Solutions, Chapter 10, pp. 358 and 365, 1988.*
Bundgaard, Design of Prodrugs, p. 1, 1985.*
Ulrich, Crystallization: 4 Crystal Characteristics, Kirk-Othmer Encyclopedia of Chemical Technology, Aug. 2002.*
Wolff, Some consideration for prodrug design, Burger's Medicinal Chemistry and Drug Discovery, 5th Edition, vol. I: Principles and Practice, pp. 975-977, 1995.*
Banker et al., Prodrugs, Modern Pharmaceutics, Third Edition, Revised and Expanded, pp. 451 and 596.*

(Continued)

Primary Examiner—Deepak Rao
(74) Attorney, Agent, or Firm—Fish & Richardson P.C.

(57) ABSTRACT

Compounds of formula (1), pharmaceutically acceptable salts, solvates and in vivo hydrolysable esters thereof, have activity as pharmaceuticals, in particular as modulators of chemokine receptor (especially CXCR2) activity, and may be in the treatment (therapeutic or prophylactic) of conditions/diseases in human and non-human animals which are exacerbated or caused by excessive or unregulated production of chemokines.

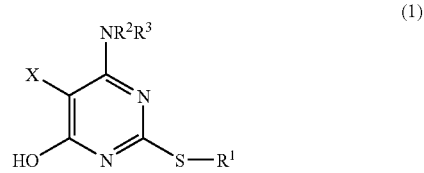

11 Claims, No Drawings

OTHER PUBLICATIONS

Cobo et al., "Reactivity of 6-Aminopyrimidin-4-(3H)-ones Towards Dimethyl Acetylenedicarboxylate (DMAD). Tandem Diels-Alder/Retro Diels-Alder (DA/RDA) Reaction in the Synthesis of 2-Aminopyridines", *Tetrahedron* 50(34):10345-10358 (1994).

Hübsch and Pfleiderer, "Synthesis and Properties of 8-Substituted 2-Thiolumazines", *Helvetica Chimica Acta* 71:1379-1391 (1988).

Lee et al., "Characterization of Two High Affinity Human Interleukin-8 Receptors", J. Biol. Chem. 267(23):16283-16287 (1992).

Merritt et al., "Use of fluo-3 to measure cytosolic $Ca^{2+}$ in platelets and neutrophils. Loading cells with the dye, calibration of traces, measurements in the presence of plasma, and buffering of cytosolic $Ca^{2+}$", *Biochem. J.* 269:513-519 (1990).

Noell and Robins, "Aromaticity in Heterocyclic Systems. II The Application of N.M.R. in a Study of the Synthesis and Structure of Certain Imidazo [1,2-c]Pyrimidines and Related Pyrrolo[2,3-d]Pyrimidines", Department of Chemistry, Arizona State University vol. 1: 34-41 (1964).

Nogimori et al., "Synthesis of 6-Anilino-2-thiouracils and Their Inhibition of Human Placenta Iodothyronine Deiodinase", *J. Med. Chem.* 28:1692-1694 (1985).

Rodriguez et al., "Aminopyrimidines and Derivatives.20. on the Acetylations of 5-Amino-4-Glycosylamino Pyrimidines", *Nucleosides & Nucleotides* 6(5):887-899 (1987).

Vinkers et al., "SYNOPSIS: Synthesis and OPtimize System in Silico", *J. Med. Chem.* 46:2765-2773 (2003).

Zambeli and Kolbah, "Acetylation of some 2-(alkyl)thio-4-amino-6-hydroxy-pyrimidines", *Acta Pharm. Jug.* 21:91-96 (1971).

Raman et al., "Role of chemokines in tumor growth", *Cancer Letters* 256:137-165 (2007).

Rosténe et al., "Chemokines: a new class of neuromodulator?", *Nature Reviews Neuroscience* 8:895-904 (2007).

* cited by examiner

PYRIMIDINE DERIVATIVES AS MODULATORS OF CHEMOKINE RECEPTOR ACTIVITY

CROSS-REFERENCE TO RELATED APPLICATIONS

This application is national phase application under 35 U.S.C. § 371 of PCT International Application No. PCT/GB2003/003632, filed Aug. 20, 2003, which claims Priority to Great Britain Application Serial No. 0219819.0, filed Aug. 24, 2002 and Great Britain Application Serial No. 0223287.4, filed Oct. 8, 2002.

The present invention relates to certain heterocyclic compounds, processes and intermediates used in their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved cysteine motif. At the present time, the chemokine superfamily comprises three groups exhibiting characteristic structural motifs, the C—X—C, C—C and C—$X_3$—C families. The C—X—C and C—C families have sequence similarity and are distinguished from one another on the basis of a single amino acid insertion between the NH-proximal pair of cysteine residues. The C—$X_3$—C family is distinguished from the other two families on the basis of having a triple amino acid insertion between the NH-proximal pair of cysteine residues.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils. Examples include human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

The C—$X_3$—C chemokine (also known as fractalkine) is a potent chemoattractant and activator of microglia in the central nervous system (CNS) as well as of monocytes, T cells, NK cells and mast cells.

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX$_3$CR1 for the C—$X_3$—C family. These receptors represent good targets for drug development since agents which modulate these receptors would be useful in the treatment of disorders and diseases such as those mentioned above.

The present invention provides compounds of formula (1), pharmaceutically acceptable salts or solvates thereof and in vivo hydrolysable esters thereof:

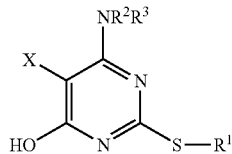

(1)

wherein $R^1$ is a group selected from $C_{3-7}$carbocyclyl, $C_{1-8}$alkyl, $C_{2-6}$alkenyl and $C_{2-6}$alkynyl; wherein the group is optionally substituted by 1, 2 or 3 substituents independently selected from fluoro, nitrile, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, phenyl or heteroaryl; wherein phenyl and heteroaryl are optionally substituted by 1, 2 or 3 substituents independently selected from halo, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_{1-6}$alkyl and trifluoromethyl;

wherein $R^2$ is $C_{3-7}$carbocyclyl, optionally substituted by 1, 2 or 3 substituents independently selected from:
(a) fluoro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$;
(b) a 3-8 membered ring optionally containing 1, 2 or 3 atoms selected from O, S, —$NR^8$ and whereby the ring is optionally substituted by $C_{1-3}$alkyl or fluoro; or
(c) phenyl or heteroaryl, each of which is optionally substituted by 1, 2 or 3 substituents independently selected from halo, cyano, nitro, —$OR^4$, —$NR^5R^6$, —$CONR^5R^6$, —$NR^8COR^9$, —$SO_2NR^5R^6$, —$NR^8SO_2R^9$, $C_{1-6}$alkyl and trifluoromethyl;

or $R^2$ is a group selected from $C_{1-8}$alkyl, $C_{2-6}$alkenyl or $C_{2-6}$alkynyl wherein the group is substituted by 1, 2 or 3 substituents independently selected from hydroxy, amino, $C_{1-6}$alkoxy, $C_{1-6}$alkylamino, di($C_{1-6}$alkyl)amino, N—($C_{1-6}$alkyl)-N-(phenyl)amino, N—$C_{1-6}$alkylcarbamoyl, N,N—($C_{1-6}$alkyl)$_2$carbamoyl, N—($C_{1-6}$alkyl)-N-(phenyl)carbamoyl, carboxy, phenoxycarbonyl, —$NR^8COR^9$, —$SO_2R^{10}$, —$SO_2NR^5R^6$ and —$NR^8SO_2R^9$;

wherein $R^3$ is hydrogen or $R^2$;

$R^4$ is hydrogen or a group selected from $C_{1-6}$alkyl and phenyl, wherein the group is optionally substituted by 1 or 2 substituents independently selected from halo, phenyl, —$OR^{11}$ and —$NR^{12}R^{13}$;

$R^5$ and $R^6$ are independently hydrogen or a group selected from $C_{1-6}$alkyl and phenyl wherein the group is optionally substituted by 1, 2 or 3 substituents independently selected from halo, phenyl, —$OR^{14}$, —$NR^{15}R^{16}$, —$CONR^{15}R^{16}$, —$NR^{15}COR^{16}$, —$SONR^{15}R^{16}$ and $NR^{15}SO_2R^{16}$ or $R^5$ and $R^6$ together with the nitrogen atom to which they are attached form a 4- to 7-membered saturated heterocyclic ring system optionally containing a further heteroatom selected from oxygen and nitrogen atoms, where the ring system may be optionally substituted by 1, 2 or 3 substituents independently selected from phenyl, —$OR^{14}$, —$COOR^{14}$, —$NR^{15}R^{16}$, —$CONR^{15}R^{16}$, —$NR^{15}COR^{16}$, —$SONR^{15}R^{16}$, $NR^{15}SO_2R^{16}$ or $C_{1-6}$alkyl (optionally substituted by 1 or 2 substituents independently selected from halo, —$NR^{15}R^{16}$ and —$OR^{17}$ groups);

$R^{10}$ is hydrogen or a group selected from $C_{1-6}$alkyl or phenyl, wherein the group is optionally substituted by 1, 2 or 3 substituents independently selected from halo, phenyl, —$OR^{17}$ and —$NR^{15}R^{16}$; and each of $R^7$, $R^8$, $R^9$, $R^{11}$, $R^{12}$, $R^{13}$, $R^{14}$ $R^{15}$, $R^{16}$, $R^{17}$ is independently hydrogen, $C_{1-6}$alkyl or phenyl;

X is hydrogen, halo, cyano, nitro, hydroxy, $C_{1-6}$alkoxy (optionally substituted by 1 or 2 substituents selected from halo, —$OR^{11}$ and —$NR^{12}R^{13}$), —$NR^5R^6$, —$COOR^7$, —$CONR^5R^6$, —$NR^8COR^9$, thio, thiocyano, thio$C_{1-6}$alkyl (optionally substituted by 1 or 2 substituents selected from halo, —$OR^{17}$, —$CO_2R^7$, —$NR^{15}R^{16}$, —$CONR^5R^6$), —$SO_2R^{10}$, —$SO_2NR^5R^6$, —$NR^8SO_2R^{10}$ or a group selected from $C_{3-7}$carbocyclyl, $C_{1-8}$alkyl, $C_{2-6}$alkenyl or $C_{2-6}$alkynyl, wherein the group is optionally substituted by 1, 2 or 3 substituents independently selected from halo, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$ and —$NR^8SO_2R^9$; or a -phenyl, -heteroaryl, -thiophenyl, -thioheteroaryl, aminoheteroaryl, and thio$C_{1-6}$ alkylheteroaryl group, all of which may be optionally substituted by 1, 2 or 3 substituents independently selected from halo, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_{1-6}$alkyl, phenyl, heteroaryl or trifluoromethyl groups.

Certain compounds of formula (1) are capable of existing in stereoisomeric forms. It will be understood that the invention encompasses all geometric and optical isomers of the compounds of formula (1) and mixtures thereof including racemates.

The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Within the present invention it is to be understood that a compound of formula (1) or a salt, solvate or in vivo hydrolysable ester thereof may exhibit the phenomenon of tautomerism and that the formulae drawings within this specification can represent only one of the possible tautomeric forms. It is to be understood that the invention encompasses any tautomeric form and mixtures thereof and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It is also to be understood that certain compounds of formula (1) and salts thereof can exist in solvated as well as unsolvated forms such as, for example, hydrated forms. It is to be understood that the invention encompasses all such solvated forms.

The present invention relates to the compounds of formula (1) as hereinbefore defined as well as to the salts thereof. Salts for use in pharmaceutical compositions will be pharmaceutically acceptable salts, but other salts may be useful in the production of the compounds of formula (1) and their pharmaceutically acceptable salts. Pharmaceutically acceptable salts of the invention may, for example, include acid addition salts of the compounds of formula (1) as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromides, phosphates, sulphates, hydrogen sulphates, alkylsulphonates, arylsulphonates, acetates, benzoates, citrates, maleates, fumarates, succinates, lactates, tartrates, oxalates, methanesulphonates or p-toluenesulphonates. Pharmaceutically acceptable salts of the invention may also include basic addition salts of the compounds of formula (1) as hereinbefore defined which are sufficiently acidic to form such salts. Such salts may be formed with an inorganic or organic base which affords a pharmaceutically acceptable cation. Such salts with inorganic or organic bases include for example an alkali metal salt, such as a lithium, sodium or potassium salt, an alkaline earth metal salt such as a calcium or magnesium salt, an ammonium salt or an organic amine salt, for example a salt with methylamine, dimethylamine, trimethylamine, triethylamine, piperidine, morpholine or tris-(2-hydroxyethyl) amine. Other basic addition salts include aluminium, zinc, benzathine, chloroprocaine, choline, diethanolamine, ethanolamine, ethyldiamine, meglumine, tromethamine or procaine.

The present invention further relates to an in vivo hydrolysable ester of a compound of formula (1). An in vivo hydrolysable ester of a compound of formula (1) which contains carboxy or hydroxy group is, for example a pharmaceutically acceptable ester which is cleaved in the human or animal body to produce the parent acid or alcohol. Such esters can be identified by administering, for example, intravenously to a test animal, the compound under test and subsequently examining the test animal's body fluid.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable pharmaceutically-acceptable esters for hydroxy include inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include $C_{1-10}$alkanoyl, for example acetyl; benzoyl; phenylacetyl; substituted benzoyl and phenylacetyl, $C_{1-10}$alkoxycarbonyl (to give alkyl carbonate esters), for example ethoxycarbonyl; di-($C_{1-4}$)alkylcarbamoyl and N-(di-($C_{1-4}$)alkylaminoethyl)-N—($C_{1-4}$)alkylcarbamoyl (to give carbamates); di-($C_{1-4}$) alkylaminoacetyl and carboxyacetyl. Examples of ring substituents on phenylacetyl and benzoyl include aminomethyl, ($C_{1-4}$)alkylaminomethyl and di-(($C_{1-4}$)alkyl)aminomethyl, and morpholino or piperazino linked from a ring nitrogen atom via a methylene linking group to the 3- or 4-position of the benzoyl ring. Other interesting in-vivo hyrolysable esters include, for example, $R^A C(O)O(C_{1-6})$alkyl-CO—, wherein $R^A$ is for example, benzyloxy-($C_{1-4}$)alkyl, or phenyl). Suitable substituents on a phenyl group in such esters include, for example, 4-($C_{1-4}$)piperazino-($C_{1-4}$)alkyl, piperazino-($C_{1-4}$) alkyl and morpholino-($C_{1-4}$)alkyl.

In this specification the term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "$C_{1-3}$alkyl" includes methyl, ethyl, propyl and isopropyl and examples of "$C_{1-6}$alkyl" include the examples of "$C_{1-3}$alkyl" and additionally t-butyl, pentyl, 2,3-dimethylbutyl, 3-methylbutyl and hexyl. Examples of "$C_{1-8}$alkyl" include the examples of "$C_{1-6}$alkyl" and additionally heptyl, 2,3-dimethylpentyl, 1-propylbutyl and octyl. An analogous convention applies to other terms, for example "$C_{2-6}$alkenyl" includes vinyl, allyl, 1-propenyl, 2-butenyl, 3-butenyl, 3-methylbut-1-enyl, 1-pentenyl and 4-hexenyl and examples of "$C_{2-6}$alkynyl" includes ethynyl, 1-propynyl, 3-butynyl, 2-pentynyl and 1-methylpent-2-ynyl.

"$C_{3-7}$carbocyclyl" is a saturated, partially saturated or unsaturated, monocyclic ring containing 3 to 7 carbon ring atoms wherein a —$CH_2$— group can optionally be replaced by a —C(O)—. Suitable examples of "carbocyclyl" are cyclopropyl, cyclopentyl, cyclobutyl, cyclohexyl, cyclohexenyl, 4-oxocyclohex-1-yl and 3-oxocyclohept-5-en-1-yl.

The term "halo" refers to fluoro, chloro, bromo and iodo.

Examples of "$C_{1-6}$alkoxy" include methoxy, ethoxy, propoxy, isopropoxy, butyloxy, pentyloxy, 1-ethylpropoxy and hexyloxy. Examples of "$C_{1-6}$alkylamino" include methylamino, ethylamino, propylamino, butylamino and 2-methylpropylmino. Examples of "di($C_{1-6}$alkyl)amino" include dimethylamino, N-methyl-N-ethylamino, diethylamino, N-propyl-N-3-methylbutylamino. Examples of "N—($C_{1-6}$alkyl)-N-(phenyl)amino" include N-methyl-N-phenylamino, N-propyl-N-phenylamino and N-(2-methylbutyl)-N-phenylamino. Examples of "N—($C_{1-6}$alkyl)carbamoyl" are N-methylcarbamoyl, N-ethylcarbamoyl and N-(2-ethylbutylcarbamoyl. Examples of "N—($C_{1-6}$alkyl)-N-(phenyl)carbamoyl" include N-methyl-N-phenylcarbamoyl, N-butyl-N-phenylcarbamoyl and N-(3-methylpentyl)-N-(phenyl)carbamoyl. Examples of "N,N-di($C_{1-6}$alkyl)carbamoyl" include N,N-dimethylcarbamoyl, N-methyl-N-ethylcarbamoyl and N-propyl-N-(2-methylbutyl)carbamoyl. Examples of "thio$C_{1-6}$alkyl" include -thiomethyl, -thioethyl, -thiopropyl, -thiobutyl and -thio-2-methylbutyl.

"Heteroaryl" is monocyclic or bicyclic aryl ring containing 5 to 10 ring atoms of which 1, 2, 3 or 4 ring atoms are chosen from nitrogen, sulphur or oxygen. Examples of heteroaryl include pyrrolyl, furanyl, thienyl, thiazolyl, isothiazolyl, oxazolyl, isoxazolyl, imidazolyl, pyrazolyl, triazolyl, tetrazolyl, oxadiazolyl, thiadiazolyl, pyridyl, thiopyridone, pyrimidinyl, pyrazinyl, pyridazinyl, triazinyl, benzfuranyl, benzthieno, indolyl, benzimidazolyl, benzoxazolyl, benzthiazolyl, indazolyl, benzisoxazolyl, benzisothiazolyl, benztriazolyl, quinolinyl, isoquinolinyl and naphthiridinyl.

Examples of "a 3-8 membered ring optionally containing 1, 2 or 3 atoms selected from O, S and $NR^8$" include azetidinyl, pyrrolidinyl, tetrahydrofuranyl, tetrahydrothiophenyl, tetrahydropyranyl, piperidinyl, piperazinyl and morpholinyl.

Examples of "a 4- to 7-membered saturated heterocyclic ring system" include azetidinlyl, pyrrolidihyl, piperidinyl, piperazinyl, homopiperazinyl and morpholinyl.

Where optional substituents are chosen from "1, 2 or 3" groups it is to be understood that this definition includes all substituents being chosen from one of the specified groups or the substituents being chosen from two or more of the specified groups. An analogous convention applies to substituents chosen from "1 or 2" groups.

Convenient values of $R^1$, $R^2$, $R^3$ and X are as follows. Such values may be used where appropriate with any of the definitions, claims or embodiments defined hereinbefore or hereinafter.

In one aspect of the present invention there is provided a compound of formula (1) as depicted above wherein $R^1$ is $C_{1-8}$alkyl optionally substituted by 1, 2 or 3 substituents independently selected from phenyl or heteroaryl, wherein phenyl and heteroaryl are optionally substituted by 1, 2 or 3 substituents independently selected from halo, cyano, —$OR^4$, —$SR^{10}$, $C_{1-6}$alkyl and trifluoromethyl.

In another aspect of the invention $R^1$ is benzyl optionally substituted by 1 or 2 substituents independently selected from fluoro, chloro, bromo, methoxy, methyl and trifluoromethyl.

In one aspect of the invention $R^2$ is $C_{1-8}$alkyl substituted by 1, 2 or 3 substituents independently selected from hydroxy, amino, $C_{1-6}$alkoxy, $C_{1-6}$alkylamino, di($C_{1-6}$alkyl)amino, N—($C_{1-6}$alkyl)-N-(phenyl)amino, N—$C_{1-6}$alkylcarbamoyl, N,N-di($C_{1-6}$alkyl)carbamoyl, N—($C_{1-6}$alkyl)-N-(phenyl)carbamoyl, carboxy, phenoxycarbonyl, —$NR^8COR^9$, —$SO_2R^{10}$, —$SO_2NR^5R^6$ and —$NR^8SO_2R^9$.

In another aspect $R^2$ is $C_{1-8}$alkyl, such as $C_{1-4}$alkyl, substituted by 1, 2 or 3 substituents independently selected from hydroxy, amino, $C_{1-6}$alkoxy, $C_{1-6}$alkylamino, and di($C_{1-6}$alkyl)amino.

In another aspect $R^2$ is $C_{1-4}$alkyl substituted by hydroxy.

In a further aspect $R^2$ is 2-hydroxy-1-methylethyl.

In one aspect of the invention $R^3$ is hydrogen.

In one aspect of the invention $R^4$ is hydrogen, $C_{1-4}$alkyl or phenyl.

In one aspect of the invention $R^5$ is hydrogen, $C_{1-4}$alkyl or phenyl.

In one aspect of the invention $R^6$ is hydrogen, $C_{1-4}$alkyl or phenyl.

In one aspect of the invention $R^{10}$ is hydrogen, $C_{1-4}$alkyl or phenyl.

In one aspect of the invention X is hydrogen, halo, cyano, nitro, hydroxy, —$NR^5R^6$, thio, thiocyano, —$CONR^5R^6$, thio$C_{1-6}$alkyl (optionally substituted by 1 or 2 substituents selected from halo, —$OR^{17}$, —$CONR^5R^6$, —$COOR^7$, —$NR^{15}R^{16}$), —$NR^8SO_2R^{10}$, $C_{1-8}$alkyl (optionally substituted by 1, 2 or 3 substituents independently selected from halo, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$ and —$NR^8SO_2R^9$) or a -phenyl, -heteroaryl, -thiophenyl, -thioheteroaryl, aminoheteroaryl, and thio$C_{1-6}$alkylheteroaryl group, all of which may be optionally substituted by 1, 2 or 3 substituents independently selected from halo, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_1$-$C_6$alkyl, phenyl, heteroaryl or trifluoromethyl groups;

In another aspect X is hydrogen, halo, cyano, nitro, hydroxy, thio, thiocyano, —$CONR^5R^6$, thio$C_{1-6}$alkyl (optionally substituted by 1 or 2 substituents selected from halo, —$OR^{17}$, —$NR^{15}R^{16}$, —$CONR^5R^6$), —$NR^8SO_2R^{10}$, $C_{1-8}$alkyl (optionally substituted by 1, 2 or 3 substituents independently selected from halo, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$ and —$NR^8SO_2R^9$), heteroaryl, thioheteroaryl or thio$C_{1-6}$alkylheteroaryl all of which may be optionally substituted by 1, 2 or 3 substituents independently selected from halo, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_{1-6}$alkyl or trifluoromethyl.

In another aspect X is hydrogen.

In another aspect X is —$CONR^5R^6$

In another aspect X is 1,2,4-oxadiazol-3-ylmethanethio

In another aspect X is $NR^8SO_2R^{10}$ where $R^8$ is hydrogen and $R^9$ is methyl.

In another aspect X is thiocyano.

In another aspect X is thiothiadazolyl, thioimidazolyl or thiotriazolyl.

In a further aspect X is fluoro, chloro or cyano

A particular class of compound is of formula (1) wherein;

$R^1$ is $C_{1-8}$alkyl optionally substituted by 1, 2 or 3 substituents independently selected from phenyl or heteroaryl, wherein phenyl and heteroaryl are optionally substituted by 1, 2 or 3 substituents independently selected from halo, cyano, —$OR^4$, —$SR^{10}$, $C_{1-6}$alkyl and trifluoromethyl;

$R^2$ is $C_{1-8}$alkyl substituted by 1, 2 or 3 substituents independently selected from hydroxy, amino, $C_{1-6}$alkoxy, $C_{1-6}$alkylamino, di($C_{1-6}$alkyl)amino, N—($C_{1-6}$alkyl)-N-phenyl)amino, N—$C_{1-6}$alkylcarbamoyl, N,N-di($C_{1-6}$alkyl)carbamoyl, N—($C_{1-6}$alkyl)-N-(phenyl)carbamoyl, carboxy, phenoxycarbonyl, —$NR^8COR^9$, —$SO_2R^{10}$, —$SO_2NR^5R^6$ and —$NR^8SO_2R^9$;

$R^3$ is hydrogen;

$R^4, R^5, R^6, R^7, R^8, R^9, R^{10}, R^{11}, R^{12}, R^{13}, R^{14} R^{15}, R^{16}$ and $R^{17}$ are independently hydrogen, $C_{1-4}$alkyl or phenyl; and X is halo, cyano, nitro, hydroxy, thio, —$NR^5R^6$, thiocyano, —$CONR^5R^6$, thio$C_{1-6}$alkyl (optionally substituted by 1 or 2 substituents selected from halo, —$OR^{17}$, —$NR^{15}R^{16}$, —$CONR^5R^6$), —$NR^8SO_2R^{10}$, $C_{1-8}$alkyl (optionally substituted by 1, 2 or 3 substituents independently selected from halo, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$ and —$NR^8SO_2R^9$);

or an aryl, heteroaryl, thioheteroaryl or thio$C_{1-6}$alkylheteroaryl all of which may be optionally substituted by 1, 2 or 3 substituents independently selected from halo, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_{1-6}$alkyl or trifluoromethyl;

A preferred class of compound is of formula (1) wherein;

$R^1$ is benzyl optionally substituted by 1 or 2 substituents independently selected from fluoro and chloro;

$R^2$ is $C_{1-4}$alkyl substituted by hydroxy;

$R^3$ is hydrogen;

X is fluoro, chloro, cyano or thioimidazolyl.

Compounds of the invention include:

2-(Benzylthio)-6-{[(1R)-2-hydroxy-1-methylethyl]amino}-4-pyrimidinol 2-(Benzylthio)-5-chloro-6-{[(1R)-2-hydroxy-1-methylethyl]amino}-4-pyrimidinol 2-[(3-Chlorobenzyl)thio]-6-{[(1R)-2-hydroxy-1-methylethyl]amino}-4-pyrimidinol 5-Chloro-2-[(3-chlorobenzyl)thio]-6-{[(1R)-2-hydroxy-1-methylethyl]amino}-4-pyrimidinol 2-[(3-Chlorobenzyl)thio]-4-hydroxy-6-{[(1R)-2-hydroxy-1-methylethyl]amino}-5-pyrimidinyl thiocyanate N-(2-[(3-Chlorobenzyl)thio]-4-hydroxy-6-{[(1R)-2-hydroxy-1-methylethyl]amino}-5-pyrimidinyl)methanesulfonamide 2-[(3-Chlorobenzyl)thio]-5-fluoro-6-{[(1R)-2-hydroxy-1-methylethyl]amino}-4-pyrimidinol 2-[(2,3-difluorobenzyl)thio]-4-hydroxy-6{[(1S)-2-hdroxy-1-methylethyl]amino}pyrimidine-5-carbonitrile 5-Chloro-2-[[(2,3-difluorophenyl)methyl]thio]-6-[[(1R)-2-hydroxy-1-methylethyl]amino]4-pyrimidinol, 2-[[(2,3-Difluorophenyl)methyl]thio]-6-[[(1R)-2-hydroxy-1-methylethyl]amino]-5-iodo-4-pyrimidinol, 2-[[(2,3-Difluorophenyl)methyl]thio]-6-[[(1R)-2-hydroxy-1-methylethyl]amino]-5-nitro-4-pyrimidinol, 2-[[(3-Chlorophenyl)methyl]thio]-6-[[(1R)2-hydroxy-1-methylethyl]amino]-5-(1,3,4-thiadiazol-2-ylthio)-4-pyrimidinol, 2-[[(2,3-Difluorophenyl)methyl]thio]-6-[[(1R)-2-hydroxy-1-methylethyl]amino]-5-(1H-imidazol-2-ylthio)-4-pyrimidinol, 2-[[(2,3-Difluorophenyl)methyl]thio]-5-[[2-(dimethylamino)ethyl]thio]-6-[[(1R)-2-hydroxy-1-methylethyl]amino]-4-pyrimidinol, 1-[2-[[(2,3-Difluorophenyl)methyl]thio]-4-hydroxy-6-[[(1R)-2-hydroxy-1-methylethyl]amino]-5-pyrimidinyl]-4(1H)-pyridinethione, 2-[[(2,3-Difluorophenyl)methyl]thio]-6-[[(1R)-2-hydroxy-1-methylethyl]amino]-5-(4-pyridinylthio)-4-pyrimidinol, 2-[[(2,3-Difluorophenyl)methyl]thio]-6-[[(1R)-2-hydroxy-1-methylethyl]amino]-5-(1H-1,2,4-triazol-3-ylthio)-4-pyrimidinol, 2-[[(2,3-Difluorophenyl)methyl]thio]-6-[[(1R)-2-hydroxy-1-methylethyl]amino]-5-[(4-methyl-4H-1,2,4-triazol-3-yl)thio]-4-pyrimidinol, 5-[(5-Amino-4H-1,2,4-triazol-3-yl)thio]-2-[[(2,3-difluorophenyl)methyl]thio]-6-[[(1R)-2-hydroxy-1-methylethyl]amino]-4-pyrimidinol, 2-[[(2,3-Difluorophenyl)methyl]thio]-6-[[(1R)-2-hydroxy-1-methylethyl]amino]-5-[[5-(4-pyridinyl)-1,3,4-oxadiazol-2-yl]thio]-4-pyrimidinol, Ethyl[[2-[[(2,3-difluorophenyl)methyl]thio]-4-hydroxy-6-[[(1R)-2-hydroxy 1-methylethyl]amino]-5-pyrimidinyl]thio]-AcOH, 2-[[2-[[(2,3-Difluorophenyl)methyl]thio]-4-hydroxy-6-[[(1R)-2-hydroxy-1-methylethyl]amino]-5-pyrimidinyl]thio]-N-methyl-acetamide, 2-[[2-[[(2,3-Difluorophenyl)methyl]thio]-4-hydroxy-6-[[(1R)-2-hydroxy-1-methylethyl]amino]-5-pyrimidinyl]thio]-N-[2-(dimethylamino)ethyl]-acetamide, 1-[[[2-[[(2,3-Difluorophenyl)methyl]thio]-4-hydroxy-6-[[(1R)-2-hydroxy-1-methylethyl]amino]-5-pyrimidinyl]thio]acetyl]-piperazine, -[[(2,3-Difluorophenyl)methyl]thio]-6-[[(1R)-2-hydroxy-1-methylethyl]amino]-5-[(4-methyl-2-oxazolyl)thio]-4-pyrimidinol, 2-[[(2,3-Difluorophenyl)methyl]thio]-6-[[(1R)-2-hydroxy-1-methylethyl]amino]-5-[(1,2,4-oxadiazol-3-ylmethyl)thio]-4-pyrimidinol, 2-[(2,3-difluorobenzyl)thio]-4-{[(1R)-1,2-dihydroxyethyl]amino}-6-hydroxypyrimidine-5-carboxamide, 2-[(2,3-difluorobenzyl)thio]-6-{[(1R)-2-hydroxy-1-methylethyl]amino}-5-(5-methyl-1,2,4-oxadiazol-3-yl)pyrimidin-4-ol, 2-[(2,3-difluorobenzyl)thio]-6-{[(1R)-2-hydroxy-1-methylethyl]amino}-5-(1,3-oxazol-5-yl)pyrimidin-4-ol, 2-[(2,3-difluorobenzyl)thio]-4-{[(1R)-1,2-dihydroxyethyl]amino}-6-hydroxy-N,N-dimethylpyrimidine-5-carboxamide, 2-[(2,3-difluorobenzyl)thio]-5-fluoro-6-{[(1R)-2-hydroxy-1-methylethyl]amino}-pyrimidin-4-ol, 2-[(3,4-difluorobenzyl)thio]-5-fluoro-6-{[(1R)-2-hydroxy-1-methylethyl]amino}-pyrimidin-4-ol, 2-[(3-fluorobenzyl)thio]-5-fluoro-6-{[(1R)-2-hydroxy-1-methylethyl]amino}pyrimidin-4-ol, or 2-[(4-fluorobenzyl)thio]-5-fluoro-6-{[(1R)-2-hydroxy-1-methylethyl]amino}pyrimidin-4-ol and pharmaceutically acceptable salts, solvates or in vivo hydrolysable esters thereof.

Each of the above mentioned compounds and the pharmaceutically acceptable salts, solvates or in vivo hydrolysable esters thereof, individually is a preferred aspect of the invention.

The present invention further provides four processes for the preparation of compounds of formula (1) as defined above which comprise:

Process 1 a) treating a compound of formula (2):

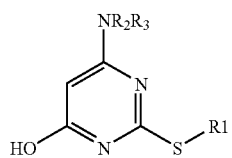

(2)

wherein $R^1$, $R^2$ and $R^3$ are as defined in formula (1), with suitable electrophiles.

and optionally thereafter (i), (ii), (iii), (iv) or (v) in any order:
i) removing any protecting groups;
ii) converting the compound of formula (1) into a further compound of formula (1),
iii) forming a salt;
(iv) forming a prodrug,
v) forming an in vivo hydrolysable ester Reaction of compounds of formula (2) wherein $R^1$, $R^2$ and $R^3$ are as defined in formula (1), with suitable electrophiles include the following representative examples: fluorination (Selectfluor™ in methanol) or chlorination, bromination or iodination (N-chlorosuccinimide, N-bromosuccinimide, N-iodosuccinimide, all in acetic acid), or chlorination (sulfulyl chloride) or bromination (bromine in N,N-diethylformamide) or thiocyanation (by in situ reaction with bromine and potassium thiocyanate) or nitrosation (sodium nitrite in acetic acid) or nitration (nitronium tetrafluoroborate in sulfolane) or electrophilic substitution with sulfenyl halides (alkyl-, aryl- or heteroarylthiols, bromine and pyridine in N,N-dimethylformamide). Further compounds of formula (1) can then be obtained by reduction of the nitro or nitroso compounds to the amine (zinc in acetic acid) and subsequent treatment with either sulfonyl chlorides or acid chlorides to yield compounds of formula (1) where X is alkyl-, aryl- or heteroarylsulfonamido- and alkyl-, aryl- or heteroarylamido- respectively. Further reactions of the brominated or iodinated compounds with aryl and heteroaryl boronic acids yield compounds of formula (1) where X is aryl or heteroaryl. Further reactions of the thiocyanated product with sodium borohydride and then alkyl halides yield compounds of formula (1) where X is -thioalkylaryl or -thioalkylheteroaryl.

Compounds of formula (2) wherein $R^1$, $R^2$ and $R^3$ are as defined in formula (1), can be prepared from compounds of formula (3) wherein $R^2$ and $R^3$ are as defined in formula (1) by treatment with alkyl halides $R^1A$, where $R^1$ is as defined in formula (1) and A is a halogen, in he presence a suitable base and solvent.

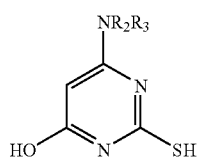

(3)

Examples of suitable bases include the alkali metal hydroxides such as Li, Na, or K, or metal carbonates such as Li, Na, K or Cs, or metal acetates such as Li, Na, K or Cs, or metal alkoxides such as Li, Na, K-tert-butoxide. Suitable solvents include N,N-dimethylamides, 1-methyl-2-pyrolidinone, ethers such as tetrahydrofuran, 1,4-dioxane, glyme and diglyme and alcohols such as methanol, ethanol and tert-butanol. Preferably potassium hydroxide in N,N-dimethylformamide at ambient temperature is employed.

Compounds of formula (3) wherein $R^2$ and $R^3$ are as defined in formula (1) may be prepared by reaction of 6-amino-2-mercapto-4-pyrimidinol with amines $HNR^2R^3$ where $R^2$ and $R^3$ are as defined in formula (1) in the presence of acetic acid at a temperature of 150-200° C.

Process 2

The present invention further provides a process for the preparation of a compound of formula (1) as defined above, where X is 1,3-oxazol-5-yl by;

b) treating a compound of formula (4):

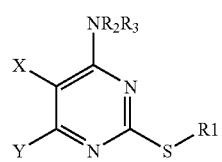

(4)

wherein $R^1$, $R^2$ and $R^3$ are as defined in formula (1), X is —CHO and Y is protected hydroxy by treatment with p-toluenesulfonylmethyl isocyanide and potassium hydroxide in refluxing methanol.

and optionally thereafter (i), (ii), (iii), (iv) or (v) in any order:
i) removing any protecting groups;
ii) converting the compound of formula (1) into a further compound of formula (1),
iii) forming a salt;
(iv) forming a prodrug,
v) forming an in vivo hydrolysable ester Compounds of formula (4) wherein $R^1$, $R^2$ and $R^3$ are as defined in formula (1), X is —CHO and Y is protected hydroxy can be prepared from compounds of formula (4) wherein $R^1$, $R^2$ and $R^3$ are as defined in formula (1), X is —CHO and Y is halogen by treatment with allyl alcohol in the presence of aqueous sodium hydroxide solution.

Compounds of formula (4) wherein $R^1$, $R^2$ and $R^3$ are as defined in formula (1), X is —CHO and Y is halogen can be prepared from compounds of formula (5) wherein $R^1$ is as defined in formula (1), X is —CHO and Y is halogen by treatment with amines $R^2R^3NH$ in the presence a suitable base and solvent.

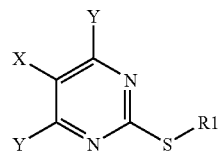

(5)

Examples of suitable bases include trialkylamines, such as triethylamine or N,N-diisopropylethylamine. Suitable solvents include N,N-diethylamides, 1-methyl-2-pyrolidone, and ethers such as tetrahydrofuran, 1,4-dioxane, glyme and diglyme. The temperature of the reaction can be performed between 0° C. and 100° C. Preferably triethylamine in N,N-dimethylformamide at room temperature is used.

Compounds of formula (5) wherein $R^1$ is as defined in formula (1), X is —CHO and Y is halogen;

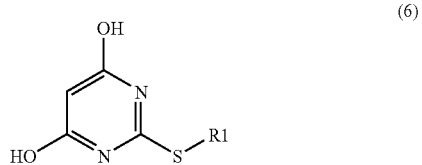

(6)

may be prepared by reaction of compounds of formula (6) wherein $R^1$ is as defined in formula (1) with a halogenating agent such as phosphorous oxychloride in the presence of N,N-dimethylformamide.

Compounds of formula (6) wherein $R^1$ is as defined in formula (1) may be prepared by reaction of 4,6-dihydroxy-2-mercaptopyrimidine with alkylhalides $R_1A$ where $R_1$ is as defined in formula (1) and A is halogen in the presence of a suitable base and solvent. Examples of suitable bases include the alkali metal hydroxides such as Li, Na, or K, or metal carbonates such as Li, Na, K or Cs, or metal acetates such as Li, Na, K or Cs, or metal alkoxides such as Li, Na, K-tert-butoxide. Suitable solvents include N,N-diethylamides, 1-methyl-2-pyrolidinone, ethers such as tetrahydrofuran, 1,4-dioxane, glyme and diglyme and alcohols such as methanol, ethanol and tert-butanol. Preferably potassium hydroxide in N,N-dimethylformamide at ambient temperature is employed.

Process 3

The present invention further provides a process for the preparation of a compound of formula (1) as defined above, where X is CN by, b) treating a compound of formula (4):

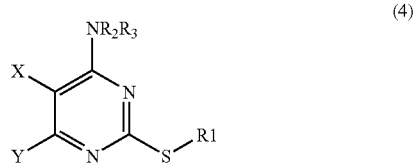

(4)

wherein $R^1$, $R^2$ and $R^3$ are as defined in formula (1), X is CN and Y is halogen by treatment with potassium tert-butoxide in refluxing aqueous toluene.

and optionally thereafter (i), (ii), (iii), (iv) or (v) in any order:
i) removing any protecting groups,
ii) converting the compound of formula (1) into a further compound of formula (1), for example treatment of a compound of formula (1) as defined above, where X is CN with hydroxylamine hydrochloride and sodium ethoxide and then acetic anhydride to provide a compound of formula (1) as defined above, where X is 5-methyl-1,2,4-oxadiazol-3-yl;
iii) forming a salt;
(iv) forming a prodrug,
v) forming an in vivo hydrolysable ester Compounds of formula (4) wherein $R^1$, $R^2$ and $R^3$ are as defined in formula (1), X is CN and Y is halogen can be prepared from compounds of formula (5) wherein $R^1$ is as defined in formula (1), X is CN and Y is halogen by treatment with amines $R^2R^3NH$ in the presence of a suitable base and solvent.

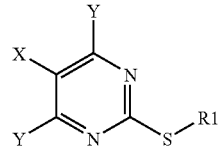

(5)

Examples of suitable bases include trialkylamines, such as triethylamine or N,N-diisopropylethylamine. Suitable solvents include N,N-dimethylamides, 1-methyl-2-pyrolidone, and ethers such as tetrahydrofuran, 1,4-dioxane, glyme and diglyme. The temperature of the reaction can be performed between 0° C. and 100° C. Preferably triethylamine in N,N-dimethylformamide at room temperature is used. Compounds of formula (5) wherein $R^1$ is as defined in formula (1), X is CN and Y is halogen may be prepared by reaction of compounds of formula (5) wherein $R^1$ is as defined in formula (1) X is —CHO and Y is halogen with hydroxylamine to form an oxime and subsequent dehydration with a dehydrating agent such as thionyl chloride. Compounds of formula (5) wherein $R^1$ is as defined in formula (1), X is —CHO and Y is halogen may be formed as described in Process (2).

Process 4

The present invention further provides a process for the preparation of a compound of formula (1) as defined above, where X is —$CONR^5R^6$ by;

c) treating a compound of formula (4):

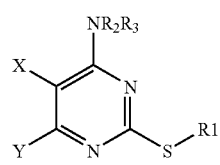

(4)

wherein $R^1$, $R^2$ and $R^3$ are as defined in formula (1), X is —$CONR^5R^6$ and Y is halogen with a suitable base.
and optionally thereafter (i), (ii), (iii), (iv) or (v) in any order:
i) removing any protecting groups;
ii) converting the compound of formula (1) into a further compound of formula (1),
iii) forming a salt;
(iv) forming a prodrug,
v) forming an in vivo hydrolysable ester Examples of suitable bases include the alkali metal hydroxides such as Li, Na, or K, or metal carbonates such as Li, Na, K or Cs, or metal acetates such as Li, Na, K or Cs, or metal alkoxides such as Li, Na, K-tert-butoxide. Suitable solvents include N,N-dimethylamides, 1-methyl-2-pyrolidinone, toluene, ethers such as tetrahydrofuran, 1,4-dioxane, glyme and diglyme and alcohols such as methanol, ethanol and tert-butanol. Preferably potassium tert-butoxide in aqueous toluene at 110° C. is used.

Compounds of formula (4) as defined above, where X is —$CONR^5R^6$ and Y is halogen can be formed by treating a compound of formula (6):

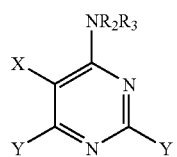

(6)

wherein $R^2$ and $R^3$ are as defined in formula (1), X is —$CONR^5R^6$ and Y is halogen with a thiol $R^1SH$, wherein $R^1$ is as defined in formula (1), in the presence of a suitable base. Examples of suitable bases include the trialkylamines, such as triethylamine or N,N-diisopropylethylamine, alkali metal hydroxides such as Li, Na, or K, or metal carbonates such as Li, Na, K or Cs, or metal acetates such as Li, Na, K or Cs, or metal alkoxides such as Li, Na, K-tert-butoxide. Suitable solvents include N,N-dimethylamides, 1-methyl-2-pyrolidinone, ethers such as tetrahydrofuran, 1,4-dioxane, glyme and diglyme and alcohols such as methanol, ethanol and tert-butanol. Preferably triethylamine in methanol at ambient temperature is used.

Compounds of formula (6) wherein $R^2$ and $R^3$ are as defined in formula (1), X is —$CONR^5R^6$ and Y is halogen can be prepared from compounds of formula (7);

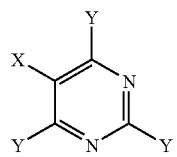

(7)

wherein X is —$CONR^5R^6$ and Y is halogen by reacting with amines $HNR^2R^3$ in the presence a suitable base and solvent.

Examples of suitable bases include the trialkylamines, such as triethylamine or N,N-diisopropylethylamine, alkali metal hydroxides such as Li, Na, or K, or metal carbonates such as Li, Na, K or Cs, or metal acetates such as Li, Na, K or Cs, or metal alkoxides such as Li, Na, K-tert-butoxide. Suitable solvents include N,N-dimethylamides, 1-methyl-2-pyrolidinone, ethers such as tetrahydrofuran, 1,4-dioxane, glyme and diglyme and alcohols such as methanol, ethanol and tert-butanol. Preferably triethylamine in N,N-dimethylformamide at −5° C. is used.

Compounds of formula (7) wherein X is —$CONR^5R^6$ and Y is halogen can be prepared from compounds of formula (7) wherein X is —COCl and Y is halogen by reacting with amines $HNR^5R^6$ in the presence a suitable base and solvent.

Examples of suitable bases include the trialkylamines, such as triethylamine or N,N-diisopropylethylamine. Suitable solvents include N,N-dimethylamides, 1-methyl-2-pyrolidinone, dichloromethane, ethers such as tetrahydrofuran, 1,4-dioxane, glyme and diglyme. Preferably sodium bicarbonate in dichloromethane at ambient temperature is used. Compounds of formula (7) wherein X is —COCl and Y is halogen can be prepared from compounds of formula (7) wherein X is —CHO and Y is halogen by treatment with aza-bis-isobutyronitrile and sulfuryl chloride in dichloroethane at 50-80° C.

Compounds of formula (7) wherein X is —CHO and Y is halogen may be prepared by reaction of 2,4,6-trihydroxypyrimidine with a halogenating agent such as phosphorous oxychloride in the presence of N,N-dimethylformamide.

It will be appreciated by those skilled in the art that in the process described above the functional groups of intermediates and starting compounds may need to be protected by protecting groups as described hereinbefore.

Compounds of formulae (2), (3), (4), (5), (6) and (7) are either commercially available, are well known in the literature or may be easily prepared using known techniques.

A compound of formula (1) may be prepared from another compound of formula (1) by chemical modification. Examples of chemical modifications include standard alkylation, arylation, heteroarylation, acylation, sulphonylation, phosphorylation, aromatic halogenation and coupling reactions. These reactions may be used to add new substituents or to modify existing substituents. Alternatively, existing substituents in compounds of formula 1 may be modified by, for example, oxidation, reduction, elimination, hydrolysis or other cleavage reactions to yield other compounds of formula (1).

The compounds of formula (1) above may be converted to a pharmaceutically acceptable salt, solvate or in vivo hydrolysable ester thereof, as discussed above. The salt is preferably a basic addition salt.

The compounds of formula (1) have activity as pharmaceuticals, in particular as modulators of chemokine receptor (especially CXCR2) activity, and may be used in the treatment (therapeutic or prophylactic) of conditions/diseases in human and non-human animals which are exacerbated or caused by excessive or unregulated production of chemokines. Examples of such conditions/diseases include:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behchet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia greata and vernal conjunctivitis;

(4) (gastrointestinal tract) Coeliac disease, proctitis, eosinopilic gastro-enteritis, mastocytosis, Crohn's disease, ulcerative colitis, indeterminate colitis, microscopic colitis, inflammatory bowel disease, irritable bowel syndrome, non-inflammatory diarrhea, endometriosis, food-related allergies which have effects remote from the gut, e.g., migraine, rhinitis and eczema;

(5) (central and peripheral nervous system) Neurodegenerative diseases and dementia disorders, e.g. Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia; polyneuropathies, e.g. Guillain-Barré syndrome, chronic inflammatory demyelinating polyradiculoneuropathy, multifocal motor neuropathy, plexopathies; CNS demyelination, e.g. multiple sclerosis, acute disseminated/haemorrhagic encephalomyelitis, and subacute sclerosing panencephalitis; neuromuscular disorders, e.g. myasthenia gravis and Lambert-Eaton syndrome; spinal disorders, e.g. tropical spastic paraparesis, and stiff-man syndrome: paraneoplastic syndromes, e.g. cerebellar degeneration and encephalomyelitis; CNS trauma; migraine; and stroke.

(6) (other tissues and systemic disease) atherosclerosis, Acquired Immunodeficiency Syndrome (AIDS), lupus erythematosus, systemic lupus, erythematosus, Hashimoto's thyroiditis, type I diabetes, nephrotic syndrome, eosinophilia fascitis, hyper IgE syndrome, lepromatous leprosy, and idiopathic thrombocytopenia pupura; postoperative adhesions, and sepsis.

(7) (allograft rejection) acute and chronic following, for example, transplantation of kidney, heart, liver, lung, bone marrow, skin and cornea; and chronic graft versus host disease;

(8) Cancers, especially non-small cell lung cancer (NSCLC), malignant melanoma, prostate cancer and squamous sarcoma, and tumour metastasis, non melanoma skin cancer and chemoprevention metastases;

(9) Diseases in which angiogenesis is associated with raised CXCR2 chemokine levels (e.g. NSCLC, diabetic retinopathy);

(10) Cystic fibrosis;

(11) Bum wounds & chronic skin ulcers;

(12) Reproductive Diseases (e.g. Disorders of ovulation, menstruation and implantation, Pre-term labour, Endometriosis);

(13) Re-perfusion injury in the heart, brain, peripheral limbs and other organs, inhibition of atherosclerosis.

Thus, the present invention provides a compound of formula (1), or a pharmaceutically-acceptable salt, solvate or an in vivo hydrolysable ester thereof, as hereinbefore defined for use in therapy.

Preferably the compounds of the invention are used to treat diseases in which the chemokine receptor belongs to the CXC chemoline chemokine receptor subfamily, more preferably the target chemokine receptor is the CXCR2 receptor.

Particular conditions which can be treated with the compounds of the invention are cancer, diseases in which angiogenesis is associated with raised CXCR2 chemokine levels, and inflammatory diseases such as asthma, allergic rhinitis, COPD, rheumatoid arthritis, psoriasis, inflammatory bowel diseases, osteoarthritis or osteoporosis.

As a further aspect of the present invention, certain compounds of formula (1) may have utility as antagonists of the CX3CR1 receptor. Such compounds are expected to be particularly useful in the treatment of disorders within the central and peripheral nervous system and other conditions characterized by an activation of microglia and/or infiltration of leukocytes (e.g. stroke/ischemia and head trauma).

In a further aspect, the present invention provides a compound of formula (1), or a pharmaceutically acceptable salt, solvate or in vivo hydrolysable ester thereof, as hereinbefore defined for use as a medicament.

In a still further aspect, the present invention provides the use of a compound of formula (1), or a pharmaceutically acceptable salt, solvate or in vivo hydrolysable ester thereof, as hereinbefore defined for use as a medicament for the treatment of human diseases or conditions in which modulation of chemokine receptor activity is beneficial.

In a still further aspect, the present invention provides the use of a compound of formula (1), or a pharmaceutically acceptable salt, solvate or in vivo hydrolysable ester thereof, as hereinbefore defined for use as a medicament for the treatment of asthma, allergic rhinitis, cancer, COPD, rheumatoid arthritis, psoriasis, inflammatory bowel diseases, osteoarthritis or osteoporosis.

In a further aspect, the present invention provides the use of a compound of formula (1), or a pharmaceutically acceptable salt, solvate or in vivo hydrolysable ester thereof, as hereinbefore defined in the manufacture of a medicament for use in therapy.

In a still further aspect, the present invention provides the use of a compound of formula (1), or a pharmaceutically acceptable salt, solvate or in vivo hydrolysable ester thereof, as hereinbefore defined in the manufacture of a medicament for the treatment of human diseases or conditions in which modulation of chemokine receptor activity is beneficial.

In a still further aspect, the present invention provides the use of a compound of formula (1), or a pharmaceutically acceptable salt, solvate or in vivo hydrolysable ester thereof, as hereinbefore defined in the manufacture of a medicament for the treatment of asthma, allergic rhinitis, cancer, COPD, rheumatoid arthritis, psoriasis, inflammatory bowel diseases, osteoarthritis or osteoporosis.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CXCR2) receptor, which comprises administering to a patient a therapeutically effective amount of a compound of formula, or a pharmaceutically acceptable salt, solvate or in vivo hydrolysable ester, as hereinbefore defined.

The invention also provides a method of treating an inflammatory disease, especially asthma, allergic rhinitis, COPD, rheumatoid arthritis, psoriasis, inflammatory bowel diseases, osteoarthritis or osteoporosis, in a patient suffering from, or at risk of, said disease, which comprises administering to the patient a therapeutically effective amount of a compound of formula (1), or a pharmaceutically acceptable salt, solvate or in vivo hydrolysable ester thereof, as hereinbefore defined.

For the above-mentioned therapeutic uses the dosage administered will, of course, vary with the compound employed, the mode of administration, the treatment desired and the disorder indicated.

The compounds of formula (1) and pharmaceutically acceptable salts, solvates or in vivo hydrolysable esters thereof may be used on their own but will generally be administered in the form of a pharmaceutical composition in which formula (1) compound/salt/solvate/ester (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (1), or a pharmaceutically acceptable salt, solvate or in vivo hydrolysable ester thereof, as hereinbefore defined, in association with a pharmaceutically acceptable adjuvant, diluent or carrier.

The invention further provides a process for the preparation of a pharmaceutical composition of the invention which comprises mixing a compound of formula (1), or a pharmaceutically acceptable salt, solvate or in vivo hydrolysable ester thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compounds of the invention are administered orally.

In addition to their use as therapeutic medicines, the compounds of formula (1) and their pharmaceutically acceptable salts, solvate or in vivo hydrolysable esters are also useful as pharmacological tools in the development and standardisation of in vitro and in vivo test systems for the evaluation of the effect of chemokine modulation activity in laboratory animals such as cats, dogs, rabbits, monkeys, rats and mice, as part of the search for new therapeutic agents.

The invention further relates to combination therapies wherein a compound of formula (1) or a pharmaceutically acceptable salt, solvate or in vivo hydrolysable ester thereof, or a pharmaceutical composition or formulation comprising a compound of formula (1) is administered concurrently or sequentially with therapy and/or an agent for the treatment of any one of asthma, allergic rhinitis, cancer, COPD, rheumatoid arthritis, psoriasis, inflammatory bowel disease, irritable bowel syndrome, osteoarthritis or osteoporosis.

In particular, for the treatment of the inflammatory diseases rheumatoid arthritis, psoriasis, inflammatory bowel disease, irritable bowel syndrome, COPD, asthma and allergic rhinitis the compounds of the invention may be combined with agents such as TNF-α inhibitors such as anti-TNF monoclonal antibodies (such as Remicade, CDP-870 and $D_2E_7$.) and TNF receptor immunoglobulin molecules (such as Enbrel.reg.), non-selective COX-1/COX-2 inhibitors (such as piroxicam, diciofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin), COX-2 inhibitors (such as meloxicam, celecoxib, rofecoxib, valdecoxib and etoricoxib) low dose methotrexate, lefunomide; ciclesonide; hydroxychloroquine, d-penicillamine, auranofin or parenteral or oral gold. For inflammatory bowel disease and irritable bowel disorder further convenient agents include sulphasalazine and 5-ASAs, topical and systemic steroids, immunomodulators and immunosuppressants, antibiotics, probiotics and anti-integrins.

The present invention still further relates to the combination of a compound of the invention together with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY x 1005.

The present invention still further relates to the combination of a compound of the invention together with a receptor antagonist for leukotrienes $LTB_4$, $LTC_4$, $LTD_4$, and $LTE_4$. selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention together with a PDE4 inhibitor including inhibitors of the isoform PDE4D.

The present invention still further relates to the combination of a compound of the invention together with a antihistaminic $H_1$. receptor antagonists such as cetirizine, loratadine, desloratadine, fexofenadine, astemizole, azelastine, and chlorpheniramine.

The present invention still further relates to the combination of a compound of the invention together with a gastroprotective $H_2$. receptor antagonist.

The present invention still further relates to the combination of a compound of the invention together with an $\alpha_1$.- and $\alpha_2$.-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the invention together with anticholinergic agents such as ipratropium bromide; tiotropium bromide; oxitropium bromide; pirenzepine; and telenzepine.

The present invention still further relates to the combination of a compound of the invention together with a $\beta_1$.-to $\beta_4$.-adrenoceptor agonists such as metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the invention together with an insulin-like growth factor type I (IGF-1) mimetic.

The present invention still further relates to the combination of a compound of the invention together with an inhaled glucocorticoid with reduced systemic side effects, such as prednisone, prednisolone, flunisolide, triamcinolone acetonide, beclomethasone dipropionate, budesonide, fluticasone propionate, and mometasone furoate.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-12.

The present invention still further relates to the combination of a compound of the invention together with other modulators of chemokine receptor function such as CCR1, CCR2, CCR2A, CCR2B, CCR3, CCR4, CCR5, CCR6, CCR7, CCR8, CCR9, CCR10 and CCR11 (for the C—C family); CXCR1, CXCR3, CXCR4 and CXCR5 (for the C—X—C family) and $CX_3CR1$ for the C—$X_3$—C family.

The present invention still further relates to the combination of a compound of the invention together with antiviral agents such as Viracept, AZT, aciclovir and famciclovir, and antisepsis compounds such as Valant.

The present invention still further relates to the combination of a compound of the invention together with cardiovascular agents such as calcium channel blockers, lipid lowering agents such as statins, fibrates, beta-blockers, Ace inhibitors, Angiotensin-2 receptor antagonists and platelet aggregation inhibitors.

The present invention still further relates to the combination of a compound of the invention together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metryfonate.

The present invention still further relates to the combination of a compound of the invention together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-$B_1$- and $B_2$-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin $NK_1$ and $NK_3$ receptor antagonists selected from the group consisting of NKP-608C; SB-233412 (talnetant); and D-4418; (xx) elastase inhibitors selected from the group consisting of UT-77 and ZD-0892; (xxi) TNFδ converting enzyme inhibitors (TACE); (xxii) induced nitric oxide synthase inhibitors (iNOS) or (xxiii) chemoattractant receptor-homologous molecule expressed on TH2 cells, (CRTH2 antagonists).

The compounds of the present invention may also be used in combination with osteoporosis agents such as roloxifene, droloxifene, lasofoxifene or fosomax and immunosuppressant agents such as FK-506, rapamycin, cyclosporine, azathioprine, and methotrexate.

The compounds of the invention may also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc and P2X7 receptor antagonists.

The compounds of the invention can also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel (Taxol®); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Pharmacological Data

Ligand Binding Assay

[$^{125}$I]IL-8 (human, recombinant) was purchased from Amersham, U.K. with a specific activity of 2,000 Ci/mmol. All other chemicals were of analytical grade. High levels of hrCXCR2 were expressed in HEK 293 cells (human embryo kidney 293 cells ECACC No. 85120602) (Lee et al. (1992) *J. Biol. Chem.* 267 pp16283-16291). hrCXCR2 cDNA was amplified and cloned from human neutrophil mRNA. The DNA was cloned into PCRScript (Stratagene) and clones were identified using DNA. The coding sequence was subcloned into the eukauyotic expression vector RcCMV (Invitrogen). Plasmid DNA was prepared using Quiagen Megaprep 2500 and transfected into HEK 293 cells using Lipofectamine reagent (Gibco BRL). Cells of the highest expressing clone were harvested in phosphate-buffered saline containing 0.2% (w/v) ethylenediaminetetraacetic acid (EDTA) and centrifuged (200 g, 5 min.). The cell pellet was resuspended in ice cold homogenisation buffer [10 mM HEPES (pH 7.4), 1 mM dithiothreitol, 1 mM EDTA and a panel of protease inhibitors (1 mM phenyl methyl sulphonyl fluoride, 2 μg/ml soybean trypsin inhibitor, 3 mM benzamidine, 0.5 μg/ml leupeptin and 100 μg/ml bacitracin)] and the cells left to swell for 10 minutes. The cell preparation was disrupted using a hand held glass mortar/PTFE pestle homogeniser and cell membranes harvested by centrifugation (45 minutes, 100,000 g, 4° C.). The membrane preparation was stored at −70° C. in homogenisation buffer supplemented with Tyrode's salt solution (137 mM NaCl, 2.7 mM KCl, 0.4 mM NaH$_2$PO$_4$), 0.1% (w/v) gelatin and 10% (v/v) glycerol.

All assays were performed in a 96-well MultiScreen 0.45 μm filtration plates (Millipore, U.K.). Each assay contained ~50 pM [$^{125}$I]IL-8 and membranes (equivalent to ~200,000 cells) in assay buffer [Tyrode's salt solution supplemented with 10 mM HEPES (pH 7.4), 1.8 mM CaCl$_2$, 1 mM MgCl$_2$, 0.125 mg/ml bacitracin and 0.1% (w/v) gelatin]. In addition, a compound of formula (I) according to the Examples was pre-dissolved in DMSO and added to reach a final concentration of 1% (v/v) DMSO. The assay was initiated with the addition of membranes and after 1.5 hours at room temperature the membranes were harvested by filtration using a Millipore MultiScreen vacuum manifold and washed twice with assay buffer (without bacitracin). The backing plate was removed from the MultiScreen plate assembly, the filters dried at room temperature, punched out and then counted on a Cobra γ-counter.

The compounds of formula (I) according to the Examples 1-34 were found to have pIC$_{50}$ values of greater than (>) 5.5. For example, Examples 3, 26 and 33 were found to have pIC$_{50}$ values of 6.10, 7.00 and 7.50 respectively.

Intracellular Calcium Mobilisation Assay

Human neutrophils were prepared from EDTA-treated peripheral blood, as previously described (Baly et al. (1997) Methods in Enzymology 287 pp70-72), in storage buffer [Tyrode's salt solution (137 mM NaCl, 2.7 mM KCl, 0.4 mM NaH$_2$PO$_4$) supplemented with 5.7 mM glucose and 10 mM HEPES (pH 7.4)].

The chemokine GROδ (human, recombinant) was purchased from R&D Systems (Abingdon, U.K.). All other chemicals were of analytical grade. Changes in intracellular free calcium were measured fluorometrically by loading neutrophils with the calcium sensitive fluorescent dye, fluo-3, as described previously (Merritt et al. (1990) Biochem. J. 269, pp513-519). Cells were loaded for 1 hour at 37° C. in loading buffer (storage buffer with 0.1% (w/v) gelatin) containing 5 μM fluo-3 AM ester, washed with loading buffer and then resuspended in Tyrode's salt solution supplemented with 5.7 mM glucose, 0.1% (w/v) bovine serum albumin (BSA), 1.8 mM CaCl$_2$ and 1 mM MgCl$_2$. The cells were pipetted into black walled, clear bottom, 96 well micro plates (Costar, Boston, U.S.A) and centrifuged (200 g, 5 minutes, room temperature).

A compound of formula (I) according to the Examples was pre-dissolved in DMSO and added to a final concentration of 0.1% (v/v) DMSO. Assays were initiated by the addition of an A$_{50}$ concentration of GROδ and the transient increase in fluo-3 fluorescence ($\delta_{Ex}$=490 nm and $\delta_{Em}$=520 nm) monitored using a FLIPR (Fluorometric Imaging Plate Reader, Molecular Devices, Sunnyvale, U.S.A.).

The compounds of formula (I) according to the Examples were tested and found to be antagonists of the CXCR2 receptor in human neutrophils.

The invention will now be illustrated by the following non-limiting examples in which, unless stated otherwise:

(i) when given Nuclear Magnetic Resonance (NMR) spectra were measured on a Varian Unity Inova 300 or 400 MHz spectrometer. $^1$H NMR data is quoted in the form of delta values for major diagnostic protons, given in parts per million (ppm) relative to tetramethylsilane (TMS) as an internal standard;

(ii) Mass Spectrometry (MS) spectra were measured on a Finnigan Mat SSQ7000 or Micromass Platform spectrometer.

(iii) the title and sub-titled compounds of the examples and methods were named using the ACD/Name program (version 4.55) from Advanced Chemical Development Inc, Canada;

(iv) Normal phase column chromatography and normal phase HPLC was conducted using a silica column. Reverse Phase High pressure liquid chromatography (HPLC) purification was performed using either a Waters Micromass LCZ with a Waters 600 pump controller, Waters 2487 detector and Gilson FC024 fraction collector or a Waters Delta Prep 4000 or a Gilson Auto Purification System, using a Symmetry, NovaPak or Ex-Terra reverse phase silica column.

(v) The following abbreviations are used:
AcOH acetic acid
DCM dichloromethane
DMF N,N-dimethylformamide
EtOAc ethyl acetate
MgSO$_4$ magnesium sulfate
THF tetrahydrofuran
H$_2$O water

EXAMPLE 1

2-(Benzylthio)-6-{[(1R)-2-hydroxy-1-methylethyl]amino}-4-pyrimidinol

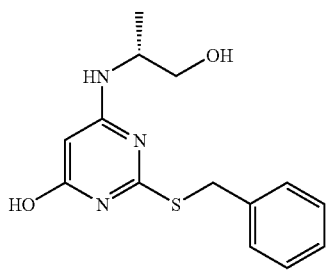

1M aqueous sodium hydroxide (6 ml) followed by benzyl bromide (0.71 ml) was added to a solution of the product of Example 1 step i) (1.0 g) in ethanol (20 ml). The mixture was stirred for 2 h, the volatiles removed under reduced pressure and the residue purified by silica gel chromatography (10% methanol/DCM) to yield the title product as a white solid. Yield 0.45 g.

MS APCI (+ve) 292 [M+H]$^+$ $^1$H NMR $\delta_{(DMSO)}$ 7.45-7.20 (5H, m), 6.72 (1H, br, d), 5.0 (1H, br, t), 4.76-4.67 (2H, br, m), 4.35 (2H, s), 3.46-3.24 (2H, m), 1.08 (3H, d).

The intermediates for this compound were prepared as follows:

i) 6-{[(1R)-2-hydroxy-1-methylethyl]amino}-2-mercapto-4-pyrimidinol

6-Amino-2-mercapto-4-pyrimidinol (16.1 g), AcOH (14.3 ml) and (R)-Alaninol (39 ml) were heated at 170° C. for 5 h. The mixture was cooled to approximately 50° C., diluted with water (500 ml) and cooled at 0° C. for 20 h. The resulting solid was filtered, washed with water and dried in vacuo to yield a mixture of subtitle product and starting material (2:1) as a cream coloured solid. Yield 7.2 g.

MS APCI (+ve) 202 [M+H]$^+$

Example 2

2-(Benzylthio)-5-chloro-6-{[(1R)-2-hydroxy-1-methylethyl]amino}-4-pyrimidinol

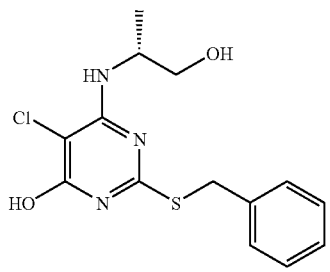

The product of Example 1 (0.5 g) was dissolved in AcOH (10 ml), N-chlorosuccinamide (0.23 g) added and stirred for 3 h. The mixture was evaporated and purified by silica gel chromatography (5% methanol/DCM) to yield the title product as a white solid. Yield 0.42 g.

MS APCI (+ve) 326 [M+H]$^+$ $^1$H NMR $\delta_{(DMSO)}$ 12.36 (1H, s), 7.44-7.22 (5H, m), 6.29 (1H, d), 4.79 (1H, t), 4.39 (2H, s), 4.25 (1H, m), 3.52-3.32 (2H, m), 1.12 (3H, d).

Example 3

2-[(3-Chlorobenzyl)thio]-6-{[(1R)-2-hydroxy-1-methylethyl]amino}-4-pyrimidinol

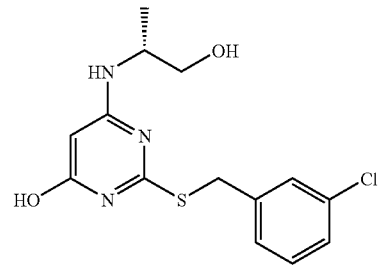

The product of Example 1 step i) (2.0 g) was dissolved in ethanol (40 ml), 1M aqueous sodium hydroxide (12 ml) added followed by 3-chlorobenzyl bromide (1.6 ml). The mixture was stirred for 2 h, the volatiles removed under reduced pressure and the residue purified by silica gel chromatography (10% methanol/DCM) to yield the title product as a white solid. Yield 1.7 g.

MS APCI (+ve) 326 [M+H]$^+$ $^1$H NMR $\delta_{(DMSO)}$ 11.39 (1H, s), 7.50 (1H, s), 7.42-7.28 (3H, m), 6.77 (1H, m), 4.99 (1H, t), 4.34 (2H, s), 3.45-3.24 (3H, m), 1.08 (3H, d)

Example 4

5-Chloro-2-[(3-chlorobenzyl)thio]-6-{[(1R)-2-hydroxy-1-methylethyl]amino}-4-pyrimidinol

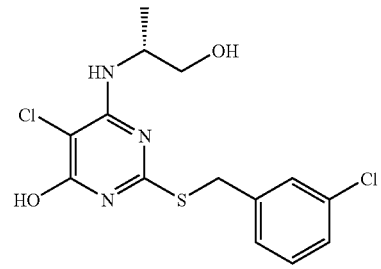

The product of Example 3 (0.22 g) was dissolved in AcOH (10 ml), N-chlorosuccinamide (90 mg) added and stirred for 3 h. The volatiles were removed under reduced pressure and the residue purified by reverse phase HPLC with gradient elution in acetonitrile/0.02M ammonium hydroxide (90% to 50% aqueous phase) to yield the title product as a white solid. Yield 0.1 g.

MS APCI (+ve) 360 [M+H]$^+$ $^1$H NMR $\delta_{(DMSO)}$ 10.33 (1H, s), 7.44-7.20 (3H, m), 6.76 (2H, d), 4.78 (1H, m), 4.34 (2H, s), 4.23 (1H, m), 3.51-3.23 (2H, m), 1.12 (3H, d).

Example 5

2-[(3-Chlorobenzyl)thio]-4-hydroxy-6-{[(1R)-2-hydroxy-1-methylethyl]amino}-5-pyrimidinyl thiocyanate

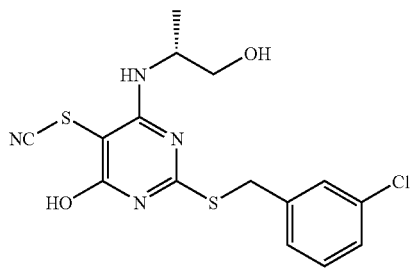

The product of Example 3 (0.5 g), pyridine (0.21 ml) and potassium thiocyanate (0.6 g) were dissolved in DMF (10 ml) and cooled to 0° C. Bromine (74 µl) was added before the cooling bath was removed and the reaction mixture allowed to warm to room temperature. After 1 h water (50 ml) was added and the mixture extracted with EtOAc (3×30 ml). The combined extracts were dried (MgSO$_4$), filtered, evaporated and purified by silica gel chromatography (10% methanol/DCM) to yield the title product as a white solid. Yield 0.3 g.

MS APCI (+ve) 383 [M+H]$^+$ $^1$H NMR $\delta_{(DMSO)}$ 12.54 (1H, s), 7.49 (1H, s), 7.15 (1H, d), 7.42-7.31 (3H, m), 4.82 (1H, m), 4.33 (1H, m), 3.53-3.36 (2H, m), 1.12 (3H, d), 4.43 (2H, m).

Example 6

N-(2-[(3-Chlorobenzyl)thio]-4-hydroxy-6-{[(1R)-2-hydroxy-1-methylethyl]amino}-5-pyrimidinyl)methanesulfonamide

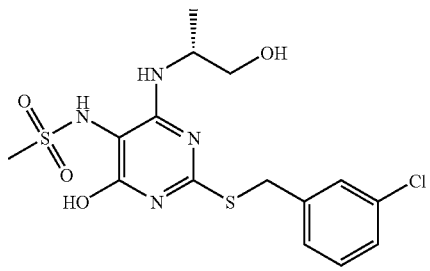

The product from Example 6 step i) (0.15 g) was dissolved in methanol (10 ml), 1M aqueous sodium hydroxide (10 ml) added and the mixture heated at 80° C. for 1 h. The mixture was cooled to room temperature, evaporated to approximately 10 ml and acidified with 2M hydrochloric acid to yield a white precipitate. The solid was filtered off, washed with water and dried to yield the title product as a white solid. Yield 0.11 g.

MS APCI (+ve) 419 [M+H]$^+$ $^1$H NMR $\delta_{(DMSO)}$ 8.31 (1H, m), 7.43-7.27 (3H, m), 7.49 (1H, s), 6.03 (1H, d), 4.80 (1H, m), 4.39 (2H, m), 4.14 (1H, m), 3.48-3.25 (2H, m), 2.96 (3H, s), 1.07 (3H, d).

i) 2-[(3-Chlorobenzyl)thio]-6-{[(1R)-2-hydroxy-1-methylethyl]amino}-5-[(methylsulfonyl)amino]4-pyrimidinyl methanesulfonate The product of Example 3 (0.9 g) was dissolved in AcOH (12 ml) and a solution of sodium nitrite (0.25 g) in water (2 ml) added dropwise to give a dark blue solution. After 10 min the mixture was evaporated, and azeotroped with ethanol (×2). The residue was dissolved in ethanol (50 ml), AcOH (2 ml) added and heated to reflux. Zinc dust (2.0 g) was added portionwise and the mixture heated at reflux for a further 5 min. The mixture was cooled to room temperature, filtered through celite and evaporated. The residue was dissolved in DMF (10 ml), treated with imidazole (0.63 g) and tert-butyldimethylsilyl chloride (1.35 g) and stirred for 24 h. The reaction was quenched with water, extracted with EtOAc (×3), dried (MgSO$_4$), filtered and evaporated. The residue was diluted in DCM (50 ml) and treated with diisopropylethylamine (4.4 ml) and methanesulfonyl chloride (0.44 ml) for 1 h before H$_2$O (10 ml) was added. The organics were recovered, dried (MgSO$_4$) and concentrated. The residue was dissolved in THF (30 ml), 1M aqueous sodium hydroxide (5 ml) added, stirred for 1 h, acidified with 2M hydrochloric acid and stirred for a further 1 h. The mixture was adjusted to pH 7 with sodium bicarbonate, extracted with EtOAc (×3), dried (MgSO$_4$), filtered and evaporated. The residue was purified by silica gel chromatography (5% methanol/DCM) to yield the subtitle product as a white solid. Yield 0.12 g.

MS APCI (+ve) 497 [M+H]$^+$ $^1$H NMR $\delta_{(DMSO)}$ 12.42 (1H, s), 7.50 (1H, s), 6.21 (1H, d), 7.43-7.32 (3H, m), 4.42 (2H, m), 4.26 (1H, m), 3.47 (3H, s), 3.44 (3H, s), 3.43 (2H, m), 1.08 (3H, d).

Example 7

2-[(3-Chlorobenzyl)thio]-5-fluoro-6-{[(1R)-2-hydroxy-1-methylethyl]amino}-4-pyrimidinol

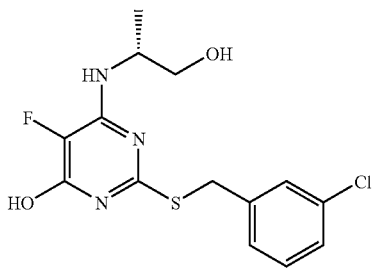

The product of Example 3 (0.1 g) was dissolved in methanol (10 ml), Selectfluor™ (0.12 g) added and stirred for 20 h. The mixture was evaporated and purified by silica gel chromatography (5% methanol/DCM) to yield the title product as a white solid. Yield 19 mg.

MS APCI (+ve) 344 [M+H]$^+$ $^1$H NMR $\delta_{(DMSO)}$ 7.48 (1H, s), 7.40-7.29 (3H, m), 6.65 (1H, t), 4.34 (2H, m), 4.13 (1H, m), 3.47-3.28 (2H, m), 1.09 (3H, d).

Example 8

2-[(2,3-difluorobenzyl)thio]-4-hydroxy-6{[(1S)-2-hdroxy-1-methylethyl]amino}-pyrimidine-5-carbonitrile

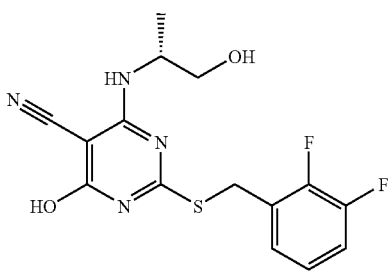

To a solution of the product of Example 8 step vi) (0.65 g) in toluene (5 ml) was added water (24 mg) and potassium tert-butoxide (0.15 g) and the mixture heated at reflux for 3 h. The reaction mixture was allowed to stand at room temperature for 16 h. The volatiles were removed in vacuo and the residue treated with methanol (50 ml) and hydrochloric acid (10 ml, 1M). The reaction mixture was stirred at room temperature for 3 h before the volatiles were removed in vacuo and the residue was neutralised by the addition of saturated sodium bicarbonate solution. This mixture was extracted with EtOAc (2×100 ml), the combined organics washed with water (2×20 ml), brine (20 ml), dried (MgSO$_4$) and concentrated to yield a yellow solid. This material was purified by column chromatography (EtOAc/isohexane (1:1) to EtOAc) to afford the title compound as a white solid. Yield 0.17 g.

MS APCI (+ve) 394 [M+CH$_3$CN]$^+$ $^1$H NMR $\delta_{(DMSO)}$ 12.63 (1H, s), 7.31-7.41 (3H, m), 7.14-7.22 (1H, m), 4.80 (1H, t), 4.41-4.60 (2H, m), 4.10-4.40 (1H, m), 3.35 (2H, m), 1.20 (3H, d).

The intermediates for this compound were prepared as follows:

i) 2-[(2,3-difluorobenzyl)thio]pyrimidine-4,6(1H,5H)-dione

Sodium hydroxide (6.1 g) in ethanol (20 ml) and water (20 ml) was added to a suspension of 4,6-dihydroxy-2-thiopyrimidine in ethanol/water (120 ml/120 ml). 2,3-difluorobenzyl bromide (28.4 g) was added dropwise to this solution. The mixture was heated at 60° C. for 2 h and stirred at room temperature for 20 h. The solids were filtered and washed with water (200 ml), isopropanol (20 ml) and dried in vacuo at 40° C. for 24 h to yield the subtitle compound. Yield 31.0 g.

MS APCI (+ve) 271 [M+H]$^+$ ii) 4,6-dichloro-2-[(2,3-difluorobenzyl)thio]pyrimidine-5-carbaldehyde

DMF (12.9 ml) was added dropwise to phosphorus oxychloride (39.6 ml) at 5° C. The resulting slurry was stirred at room temperature for 2 h. The product of Example 8 step i) was added in portions and stirred at room temperature for 1 h. The mixture was then heated at 100° C. for 12 h. The residue was concentrated in vacuo and suspended in water/ice (1:1). The solid formed was extracted with EtOAc (2×150 ml). The EtOAc layers were washed with water (2×100 ml), brine (100 ml) and dried (MgSO$_4$). The solid was filtered and the filtrate concentrated in vacuo to yield a yellow solid. This was purified by column chromatography using EtOAc/isohexane (1:9) to yield the subtitle compound. Yield 5.0 g.

$^1$H NMR $\delta_{(CDCl_3)}$ 10.37 (1H, s), 7.21-7.31 (1H, d), 7.00-7.20 (2H, m), 4.48 (2H, s).

4,6-dichloro-2-[(2,3-difluorobenzyl)thio]pyrimidine-5-carbaldehyde oxime

Hydroxylamine hydrochloride (0.99 g) was added to a slurry of the product of Example 8 step ii) (5.0 g) in water (1.34 ml) and AcOH (21 ml). This mixture was then heated at 60° C. for 3 h. The reaction mixture was then allowed to come to room temperature and water (20 ml) added before cooling to 0° C. for 1 h and then filtering. The solid obtained was purified by column chromatography eluting with DCM to yield the subtitle compound as a white solid. Yield 1.5 g.

MS APCI (+ve) 351 (M+H)$^+$ iv) 4,6-dichloro-2-[(2,3-difluorobenzyl)thio]pyrimidine-5-carbonitrile

The product of Example 8 step iii) (1.5 g) in thionyl chloride (50 ml) was heated at reflux for 4 h. The solvent was removed under reduced pressure and the residue taken up in EtOAc (2×50 ml) and concentrated under reduced pressure to yield the subtitle compound. Yield 1.5 g.

$^1$H NMR $\delta_{(CDCl_3)}$ 7.20-7.30 (1H, m), 7.26-7.31 (1H, s), 7.00-7.20 (2H, m), 4.45 (2H, s).

v) 4-chloro-2-[2,3-difluorobenzyl)thio]-6-{[(1S)-2-hydroxy-1-methylethyl]-amino}pyrimidine-5-carbonitrile (R)-Alaninol (0.96 g) in DMF (5 ml) was added dropwise at 0° C. to a solution of the product of Example 8 step iv) (1.5 g) in DMF (20 ml). The mixture was stirred at room temperature for 30 min and triethylamine (0.45 g) added at 0° C. The mixture was stirred at room temperature for 16 h. To the mixture was added water (30 ml) and extracted with EtOAc (2×100 ml). The combined organics were washed with water (2×20 ml), brine (20 ml) and dried (MgSO$_4$). The solid was filtered and the filtrate concentrated in vacuo to give a yellow solid. The solid was purified by column chromatography (30% to 50% EtOAc/isohexane) to yield the subtitle compound as a yellow solid. Yield 1.10 g.

MS APCI (+ve) 371 (M+H)$^+$ $^1$H NMR $\delta_{(DMSO)}$ 8.03 (1H, d), 7.31-7.4 (2H, m), 7.13-7.20 (1H, m), 4.77 (1H, t), 4.44 (2H, d), 4.28-4.40 (1H, m), 3.35-3.50 (2H, m), 1.15 (3H, d).

vi) 4-[(1S)-2-{[tert-butyl(dimethyl)silyl]oxy}-1-methylethyl)amino]-6-chloro-2-[(2,3-difluorobenzyl)thio]pyrimidine-5-carbonitrile Imidazole (0.20 g) was added to a solution of the product of Example 8 step v) (1.10 g) and tert-butyldimethylsilyl chloride (0.45 g) in DMF (10 ml) at 0° C. This solution was allowed to warm to room temperature and stirred for 16 h. To this mixture were added imidazole (20 mg) and tert-butyldimethylsilyl chloride (44 mg) and the mixture stirred for 2 h before water (50 ml) was added and extracted with EtOAc (2×100 ml). The combined organics were washed with water (3×30 ml), brine (30 ml), dried (MgSO$_4$), filtered and the filtrate evaporated in vacuo to yield a yellow solid. This was purified by column chromatography (isohexane and then DCM) to yield the subtitle compound as a yellow oil. Yield 0.90 g.

MS APCI (+ve) 485 (M+H)⁺

Example 9

5-Chloro-2-[[(2,3-difluorophenyl)methyl]thio]-6-[[(1R)-2-hydroxy-1-methylethyl]amino]-4-pyrimidinol

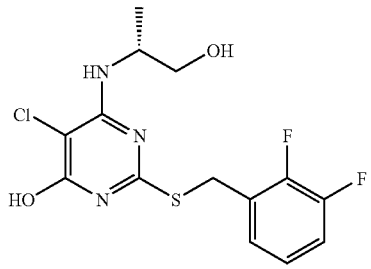

Sulphuryl chloride (27 µl) was added to a solution of the subtitle product of example 9 step ii) (0.1 g) in DMF (1 ml) and the mixture stirred for 1 h. 1 M aqueous sodium hydroxide solution (1 ml) was then added and the reaction stirred for a further 2 h. The mixture was acidified with 1M hydrochloric acid, extracted with EtOAc (2×10 ml), dried (MgSO$_4$), filtered and the filtrate evaporated in vacuo. The residue was purified by column chromatography (5% methanol/DCM) to yield the title product as a white solid. Yield 50 mg.

MS APCI (+ve) 362 [M+H]⁺

¹HNMR δ$_{(DMSO)}$ 12.53-12.36 (1H, m), 7.41-7.29 (2H, m), 7.18 (1H, m), 6.32 (1H, d), 4.79 (1H, t), 4.46 (2H, dd), 4.20 (1H, m), 3.48-3.31 (2H, m), 1.08 (3H, d)

The intermediates for this compound were prepared as follows:

i) 2-[[(2,3-Difluorophenyl)methyl]thio]-6-[[(1R)-2-hydroxy-1-methylethyl]amino]-4-pyrimidinol The subtitle product of Example 1 step i) (5.0 g) was dissolved in ethanol (100 ml), 1M aqueous sodium hydroxide (27.4 ml) added followed by 2,3-difluorobenzyl bromide (5.7 g). The mixture was stirred for 1 h, the volatiles removed under reduced pressure and the residue purified by column chromatography (5% methanol/DCM) to yield the subtitle product as a white solid. Yield 4.3 g.

MS APCI (+ve) 328 [M+H]⁺

¹H NMR δ$_{(DMSO)}$ 7.41-7.28 (2H, m), 7.15 (1H, m), 6.86-6.69 (1H, m), 5.10-4.93 (1H, m), 4.71 (1H, t), 4.41 (2H, s), 3.40 (1H, m), 3.34-3.23 (2H, m), 1.07 (3H, d)

ii) 6-[[(1R)-2-Acetyloxy)-1-methylethyl]amino]-2-[[(2,3-difluorophenyl)methyl]thio]-4-pyrimidinol Acetic anhydride (0.9 ml) was added dropwise to a solution of the subtitle product of Example 9 step i) (2.8 g), pyridine (1.6 ml) and DMAP (0.1 g) in AcOH (30 ml). Two more portions of acetic anhydride (0.9 ml) were added and the mixture stirred for 20 h. The volatiles were removed under reduced pressure and the residue purified by column chromatography (5% methanol/DCM) to yield the subtitle product as a colourless oil. Yield 3.0 g.

MS APCI (+ve) 370 [M+H]⁺

¹H NMR δ$_{(DMSO)}$ 11.60-11.37 (1H, m), 7.41-7.28 (2H, m), 7.16 (1H, m), 7.06-6.95 (1H, m), 5.07 (1H, s), 4.42 (2H, s), 3.96 (2H, d), 1.99 (3H, s), 1.11 (3H, d)

Example 10

2-[[(2,3-Difluorophenyl)methyl]thio]-6-[[(1R)-2-hydroxy-1-methylethyl]amino]-5-iodo-4-pyrimidinol

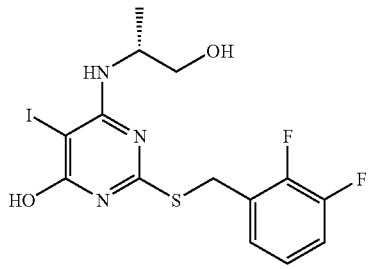

N-iodosuccinamide (0.34 g) was added to a solution of the subtitle product from Example 9 step i) (0.5 g) in AcOH (10 ml) and stirred for 2 h. The AcOH was evaporated in vacuo and the residue purified by column chromatography (5% methanol/DCM) to yield the title product as a white solid. Yield 0.42 g.

MS APCI (+ve) 453 [M+H]⁺

¹H NMR δ$_{(DMSO)}$ 12.42-12.31 (1H, m), 7.40-7.30 (2H, m), 7.18 (1H, m), 5.79 (1H, d), 4.91 (1H, t), 4.47 (2H, dd), 4.15 (1H, m), 3.46-3.39 (2H, m), 1.08 (3H, d)

Example 11

2-[[(2,3-Difluorophenyl)methyl]thio]-6-[[(1R)-2-hydroxy-1-methylethyl]amino]-5-nitro-4-pyrimidinol

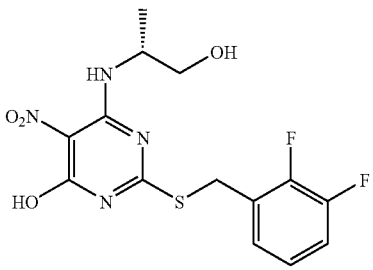

1M aqueous sodium hydroxide (1 ml) was added to a solution of the product from Example 11 step i) in methanol (10 ml) and the mixture stirred for 2 h. The mixture was diluted with water (20 ml) and acidified with 2M hydrochloric acid (2 ml) to give a red precipitate. The solid was filtered off, washed with water and dried to yield the title product as a red solid. Yield 0.15 g.

MS APCI (+ve) 453 [M+H]⁺

¹H NMR δ$_{(DMSO)}$ 12.77 (1H, s), 9.63 (1H, d), 7.47-7.29 (2H, m), 7.21 (1H, m), 5.09 (1H, t), 4.55 (2H, dd), 4.40 (1H, m), 3.49 (2H, m), 1.14 (3H, d)

The intermediates for this compound were prepared as follows:

i) 6-[[(1R)-2-(Acetyloxy)-1-methylethyl]amino]-2-[[(2,3-difluorophenyl)methyl]thio]-5-nitro-4-pyrimidinol A 0.5M solution of nitronium tetrafluoroborate in sulpholane (6.9 ml) was added dropwise to a solution of the product from Example 9 step ii) (1.0 g) in acetonitrile (30 ml) and the mixture stirred for 20 h. The acetonitrile was evaporated in vacuo and the remaining solution diluted with water (150 ml) to give a lilac precipitate. The solid was filtered off, washed with water and dried to yield the subtitle product as a lilac solid. Yield 0.85 g.

MS APCI (+ve) 415 [M+H]+

1H NMR δ(DMSO) 12.84 (1H, s), 9.47 (1H, d), 7.45-7.29 (2H, m), 7.20 (1H, m), 4.70 (1H, m), 4.54 (2H, s), 4.19-4.06 (2H, m), 1.99 (3H, s), 1.20 (3H, d)

Example 12

2-[[(3-Chlorophenyl)methyl]thio]-6-[[(1R)2-hydroxy-1-methylethyl]amino]-5-(1,3,4-thiadiazol-2-ylthio)-4-pyrimidinol

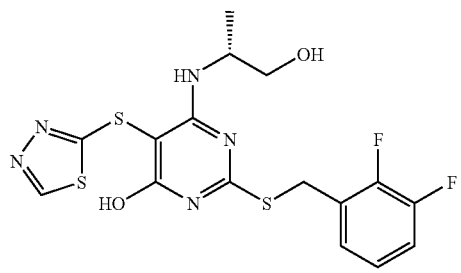

The product of Example 3 (0.12 g), pyridine (50 μl) and 1,3,4-thiadiazole-2-thiol (0.18 g) were dissolved in DMF (3 ml) and bromine (18 μl) added dropwise. The reaction mixture was stirred for 1 h before being purified directly by reverse phase HPLC (95-75% 0.02M ammonium hydroxide/acetonitrile) to yield the title product as a white solid. Yield 0.15 g.

MS APCI (+ve) 442 [M+H]+

1H NMR δ(DMSO) 12.47 (1H, s), 9.36 (1H, s), 7.51 (1H, s), 7.43-7.32 (3H, m), 7.09 (1H, d), 4.77 (1H, t), 4.45 (2H, dd), 4.31 (1H, m), 3.47-3.28 (2H, m), 1.06 (3H, d)

Example 13

2-[[(2,3-Difluorophenyl)methyl]thio]-6-[[(1R)-2-hydroxy-1-methylethyl]amino]-5-(1H-imidazol-2-ylthio)-4-pyrmidinol

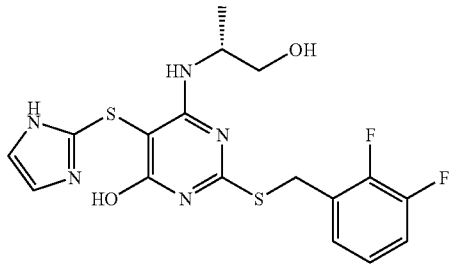

The product of Example 9 step i) (0.1 g), pyridine (0.15 ml) and 1H-imidazole-2-thiol (0.15 g) were dissolved in DMF (1 ml) and bromine (15 μl) added dropwise. The reaction mixture was stirred for 1 h before being purified directly by reverse phase HPLC (95-25% 0.02M ammonium hydroxide/acetonitrile) to yield the title product as a white solid. Yield 90 mg.

MS APCI (+ve) 426 [M+H]+

1H NMR δ(DMSO) 7.41-7.30 (2H, m), 7.18 (1H, m), 7.02-6.86 (2H, m), 6.75 (1H, d), 5.02-4.88 (1H, m), 4.48 (2H, dd), 4.21 (1H, m), 3.45-3.25 (2H, m), 1.06 (3H, d)

Example 14

2-[[(2,3-Difluorophenyl)methyl]thio]-5-[[2-dimethylamino)ethyl]thio]-6-[[(1R)-2-hydroxy-1-methylethyl]amino]-4-pyrimidinol

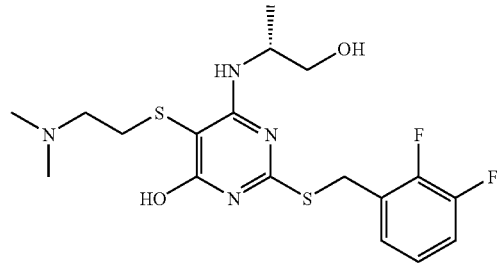

The product of Example 9 step i) (50 mg), pyridine (75 μl) and 2-(dimethylamino)ethanethiol (85 mg) were dissolved in DMF (0.5 ml) and bromine (7.5 μl) added. The reaction mixture was stirred for 1 h before being purified directly by reverse phase HPLC (95-25% 0.02M ammonium hydroxide/acetonitrile) to yield the title product as a white solid. Yield 30 mg.

MS APCI (+ve) 431 [M+H]+

1H NMR δ(DMSO) 7.42-7.29 (2H, m), 7.18 (1H, m), 6.64 (1H, d), 4.96-4.75 (1H, m), 4.45 (2H, dd), 4.17 (1H, m), 3.61-3.22 (2H, m), 2.93-2.58 (4H, m), 2.51 (6H, s), 1.10 (3H, d)

Example 15

1-[2-[[(2,3-Difluorophenyl)methyl]thio]-4-hydroxy-6-[[(1R)-2-hydroxy-1-methylethyl]amino]-5-pyrimidinyl]-4(1H)-pyridinethione

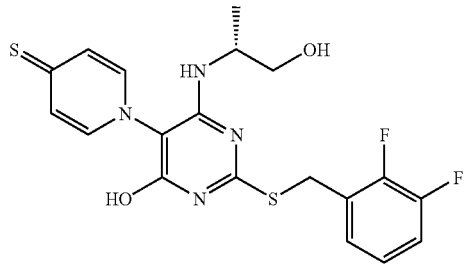

The product of Example 9 step i) (50 mg), pyridine (75 μl) and 4-pyridinethiol (75 mg) were dissolved in DMF (0.5 ml) and bromine (7.5 μl) added. The reaction mixture was stirred for 1 h before being purified directly by reverse phase HPLC (95-25% 0.02M ammonium hydroxide/acetonitrile) to yield the title product as a white solid. Yield 5 mg.

MS APCI (+ve) 437 [M+H]$^+$ $^1$H NMR $\delta_{(DMSO)}$ 8.35 (2H, d), 7.42-7.34 (2H, m), 7.26 (1H, m), 7.14 (2H, d), 7.02 (1H, d), 4.54 (2H, dd), 4.51 (1H, m), 3.79-3.65 (2H, m), 1.06 (3H, d)

Example 16

2-[[(2,3-Difluorophenyl)methyl]thio]-6-[[(1R)-2-hydroxy-1-methylethyl]amino]-5-(4-pyridinylthio)-4-pyrimidinol

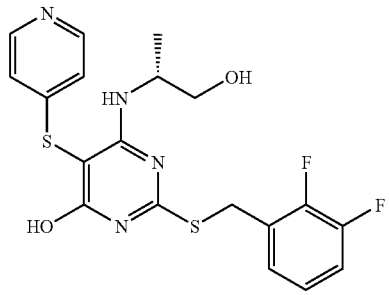

The product of Example 9 step i) (50 mg), pyridine (75 μl) and 4-pyridinethiol (75 mg) were dissolved in DMF (0.5 ml) and bromine (7.5 μl) added. The reaction mixture was stirred for 1 h before being purified directly by reverse phase HPLC (95-25% 0.02M ammonium hydroxide/acetonitrile) to yield the title product as a white solid. Yield 31 mg.

MS APCI (+ve) 437 [M+H]$^+$ $^1$H NMR $\delta_{(DMSO)}$ 8.28 (2H, d), 7.40-7.30 (2H, m), 7.18 (1H, m), 6.98 (2H, d), 4.75 (1H, m), 4.44 (2H, dd), 4.15 (1H, m), 3.40-3.25 (2H, m), 1.01 (3H, d)

Example 17

2-[[(2,3-Difluorophenyl)methyl]thio]-6-[[(1R)-2-hydroxy-1-methylethyl]amino]-5-(1H-1,2,4-triazol-3-ylthio)-4-pyrimidinol

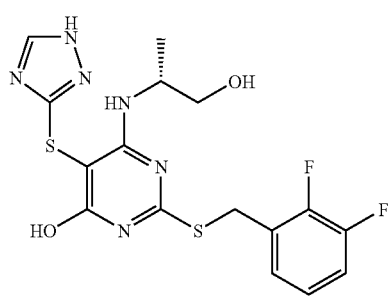

The product of Example 9 step i) (50 mg), pyridine (75 μl) and 1H-1,2,4-triazole-3-thiol (61 mg) were dissolved in DMF (0.5 ml) and bromine (7.5 μl) added. The reaction mixture was stirred for 1 h before being purified directly by reverse phase HPLC (95-25% 0.02M ammonium hydroxide/acetonitrile) to yield the title product as a white solid. Yield 32 mg.

MS APCI (+ve) 427 [M+H]$^+$ $^1$H NMR $\delta_{(DMSO)}$ 12.44-12.06 (1H, m), 7.41-7.32 (2H, m), 7.20 (1H, m), 6.68-6.49 (1H, m), 4.87-4.73 (1H, m), 4.50 (2H, dd), 4.23 (1H, m), 3.45-3.26 (2H, m), 1.04 (3H, d)

Example 18

2-[[(2,3-Difluorophenyl)methyl]thio]-6-[[(1R)-2-hydroxy-1-methylethyl]amino]-5-[(4-methyl-4H-1,2,4-triazol-3-yl)thio]-4-pyrimidinol

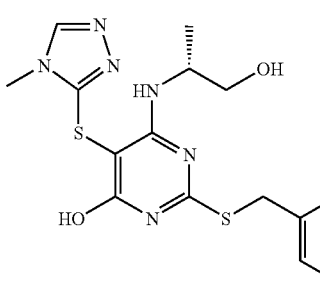

The product of Example 9 step i) (50 mg), pyridine (75 μl) and 4-methyl-4H-1,2,4-triazole-3-thiol (69 mg) were dissolved in DMF (0.5 ml) and bromine (7.5 μl) added. The reaction mixture was stirred for 1 h before being purified directly by reverse phase HPLC (95-25% 0.02M ammonium hydroxide/acetonitrile) to yield the title product as a white solid. Yield 42 mg.

MS APCI (+ve) 441 [M+H]$^+$ $^1$H NMR $\delta_{(DMSO)}$ 12.33 (1H, s), 8.51 (1H, s), 7.41-7.28 (2H, m), 7.18 (1H, m), 6.75 (1H, d), 4.88 (1H, t), 4.47 (2H, dd), 4.19 (1H, m), 3.47-3.26 (2H, m), 1.07 (3H, d)

Example 19

5-[(5-Amino-4H-1,2,4-triazol-3-yl)thio]-2-[[(2,3-difluorophenyl)methyl]thio]-6-[[(1R)-2-hydroxy-1-methylethyl]amino]-4-pyrimidinol

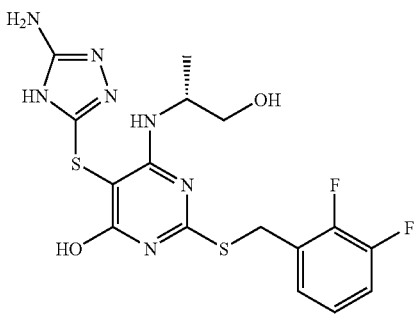

The product of Example 9 step i) (50 mg), pyridine (75 μl) and 5-amino-4H-1,2,4-triazole-3-thiol (70 mg) were dissolved in DMF (0.5 ml) and bromine (7.5 μl) added. The reaction mixture was stirred for 1 h before being purified directly by reverse phase HPLC (95-25% 0.02M ammonium hydroxide/acetonitrile) to yield the title product as a white solid. Yield 23 mg.

MS APCI (+ve) 442 [M+H]$^+$ $^1$HNMR δ$_{(DMSO)}$ 7.43-7.29 (2H, m), 7.19 (1H, m), 6.46 (1H, d), 6.06-5.89 (2H, m), 4.83 (1H, t), 4.47 (2H, dd), 4.17 (1H, m), 3.46-3.25 (2H, m), 1.04 (3H, d)

Example 20

2-[[(2,3-Difluorophenyl)methyl]thio]-6-[[(1R)-2-hydroxy-1-methylethyl]amino]-5-[[5-(4-pyridinyl)-1,3,4-oxadiazol-2-yl]thio]-4-pyrimidinol

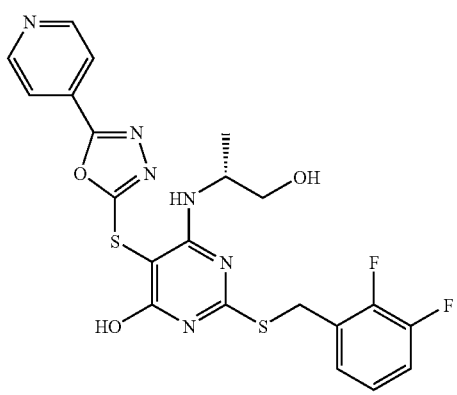

The product of Example 9 step i) (50 mg), pyridine (75 μl) and 5-(4-pyridinyl)-1,3,4-oxadiazole-2-thiol (50 mg) were dissolved in DMF (0.5 ml) and bromine (7.5 μl) added. The reaction mixture was stirred for 1 h before being purified directly by reverse phase HPLC (95-25% 0.02M ammonium hydroxide/acetonitrile) to yield the title product as a white solid. Yield 10 mg.

MS APCI (+ve) 505 [M+H]$^+$ $^1$H NMR δ$_{(DMSO)}$ 12.49 (1H, s), 8.81 (2H, d), 7.83 (2H, d), 7.43-7.34 (2H, m), 7.21 (1H, m), 7.03 (1H, d), 4.75 (1H, t), 4.54 (2H, dd), 4.33 (1H, m), 3.47-3.26 (2H, m), 1.06 (3H, d)

Example 21

Ethyl [[2-[[(2,3-difluorophenyl)methyl]thio]-4-hydroxy-6-[[(1R)-2-hydroxy-1-methylethyl]amino]-5-pyrimidinyl]thio]-AcOH

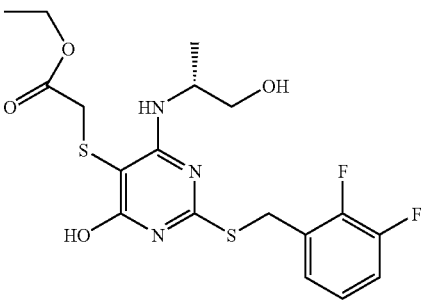

The product of Example 9 step i) (0.5 g), pyridine (0.75 ml) and 5-(4-pyridinyl)-1,3,4-oxadiazole-2-thiol (0.66 ml) were dissolved in DMF (5 ml) and bromine (75 μl) added and stirred for 1 h. The mixture was quenched with water, extracted with EtOAc (2×30 ml), dried (MgSO$_4$), filtered and the volatiles removed by evaporation in vacuo. The residue was purified by silica gel chromatography (5% methanol/EtOAc) to yield the title product as a white solid. Yield 0.25 g.

MS APCI (+ve) 446 [M+H]$^+$ $^1$HNMR δ$_{(DMSO)}$ 12.22 (1H, s), 7.41-7.29 (2H, m), 7.18 (1H, m), 6.51 (1H, d), 4.85 (1H, t), 4.47 (2H, dd), 4.15 (1H, m), 3.98 (2H, q), 3.47-3.26 (2H, m), 3.31 (2H, dd), 1.09 (3H, t), 1.08 (3H, d)

Example 22

2-[[2-[[(2,3-Difluorophenyl)methyl]thio]-4-hydroxy-6-[[(1R)-2-hydroxy-1-methylethyl]amino]-5-pyrimidinyl]thio]-N-methyl-acetamide

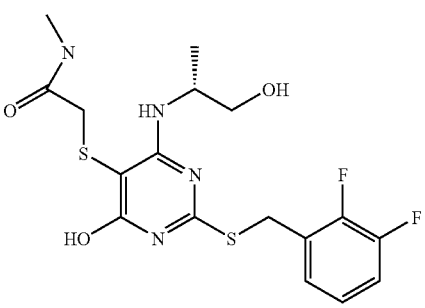

The product of Example 21 (0.1 g) was dissolved in ethanol (10 ml), 40% aqueous methylamine (2 ml) was added and the mixture stirred for 20 h. The volatiles were removed by evaporation in vacuo and the residue purified by reverse phase HPLC (95-25% 0.02M ammonium hydroxide/acetonitrile) to yield the title product as a white solid. Yield 0.1 g.

MS APCI (+ve) 431 [M+H]$^+$

¹H NMR δ(DMSO) 8.27 (1H, s), 7.40-7.29 (2H, m), 7.18 (1H, m), 6.79 (1H, d), 4.79 (1H, t), 4.46 (2H, dd), 4.17 (1H, m), 3.47-3.30 (2H, m), 3.16 (2H, s), 2.55 (3H, d), 1.08 (3H, d)

Example 23

2-[[2-[[(2,3-Difluorophenyl)methyl]thio]4-hydroxy-6-[[(1R)-2-hydroxy-1-methylethyl]amino]-5-pyrimidinyl]thio]-N-[2-(dimethylamino)ethyl]-acetamide

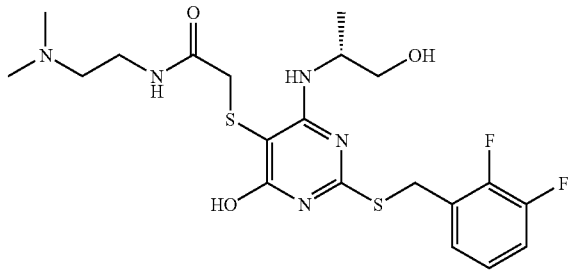

The product of Example 21 (50 mg) was dissolved in ethanol (10 ml), N,N-dimethyl-1,2-ethanediamine (0.5 ml) was added and the mixture stirred for 48 h. The volatiles were removed by evaporation in vacuo and the residue purified by reverse phase HPLC (95-25% 0.02M ammonium hydroxide/acetonitrile) to yield the title product as a white solid. Yield 30 mg.

MS APCI (+ve) 488 [M+H]⁺

¹HNMR δ(DMSO) 8.52 (1H, s), 7.39-7.29 (2H, m), 7.16 (1H, m), 6.63 (1H, d), 4.90-4.70 (1H, m), 4.43 (2H, dd), 4.13 (1H, m), 3.47-3.25 (2H, m), 3.13 (2H, q), 2.30 (2H, t), 2.16 (2H, s), 1.09 (3H, d)

Example 24

1-[[[2-[[(2,3-Difluorophenyl)methyl]thio]-4-hydroxy-6-[[(1R)-2-hydroxy-1-methylethyl]amino]-5-pyrimidinyl]thio]acetyl]-piperazine

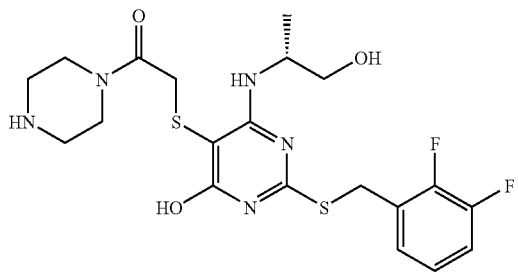

The product of example 21 (50 mg) was dissolved in methanol (10 ml), piperazine (0.5 ml) was added and the mixture heated at 40° C. for 20 h. The volatiles were removed by evaporation in vacuo and the residue purified by reverse phase HPLC (95-25% 0.02M ammonium hydroxide/acetonitrile) to yield the title product as a white solid. Yield 20 mg.

MS APCI (+ve) 486 [M+H]⁺

¹HNMR δ(DMSO) 7.39-7.29 (2H, m), 7.18 (1H, m), 6.56 (1H, d), 4.88-4.77 (1H, m), 4.45 (2H, dd), 4.11 (1H, m), 3.46-3.27 (6H, m), 3.42 (2H, s), 2.69-2.53 (4H, m), 1.07 (3H, d)

Example 25

2-[[(2,3-Difluorophenyl)methyl]thio]-6-[[(1R)-2-hydroxy-1-methylethyl]amino]-5-[(4-methyl-2-oxazolyl)thio]-4-pyrimidinol

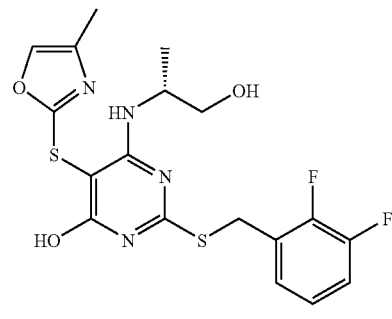

The product of Example 9 step i) (50 mg), pyridine (75 µl) and 4-methyl-2-oxazolethiol (69 mg) were dissolved in DMF (0.5 ml) and bromine (7.5 µl) added. The reaction mixture was stirred for 1 h before being purified directly by reverse phase HPLC (95-25% 0.02M ammonium hydroxide/acetonitrile) to yield the title product as a white solid. Yield 21 mg.

MS APCI (+ve) 439 [M+H]⁺

¹H NMR δ(DMSO) 7.71 (1H, s), 7.49 (1H, s), 7.42-7.30 (3H, m), 4.77 (1H, t), 4.38 (2H, dd), 4.22 (1H, m), 3.45-3.24 (2H, m), 2.00 (3H, s), 1.05 (3H, d)

Example 26

2-[[(2,3-Difluorophenyl)methyl]thio]-6-[[(1R)-2-hydroxy-1-methylethyl]amino]-5-[(1,2,4-oxadiazol-3-ylmethyl)thio]-4-pyrimidinol

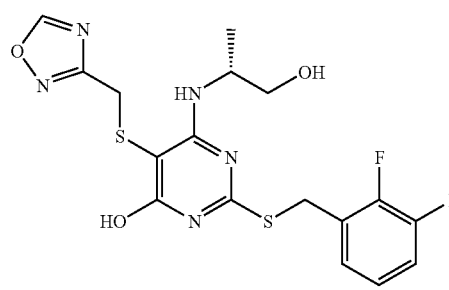

The product of Example 5 (0.2 g) was dissolved in ethanol (10 ml), sodium borohydride (20 mg) added and the reaction stirred for 1 h. 1M sodium hydroxide solution (2 ml) was then added, followed by 3-(chloromethyl)-1,2,4-oxadiazole (62 mg). The mixture was stirred for 2 h, acidified with 10% hydrochloric acid, extracted with EtOAc (2×20 ml), dried (MgSO₄), filtered and the filtrate evaporated in vacuo. The residue was purified by reverse phase HPLC with gradient elution in acetonitrile/0.02M ammonium hydroxide (95% to 25% aqueous phase, Ex-Terra) to yield the title product as a white solid. Yield 20 mg.

MS APCI (+ve) 442 [M+H]⁺

$^1$H NMR $\delta_{(DMSO)}$ 12.21 (1H, s), 9.47 (1H, s), 7.41-7.27 (2H, m), 7.18 (1H, m), 6.18 (1H, m), 4.79 (1H, t), 4.44 (2H, dd), 4.06 (1H, m), 3.84 (2H, dd), 3.38-3.23 (2H, m), 0.94 (3H, d)

Example 27

2-[(2,3-difluorobenzyl)thio]-4-{[(1R)-1,2-dihydroxyethyl]amino}-6-hydroxypyrimidine-5-carboxamide

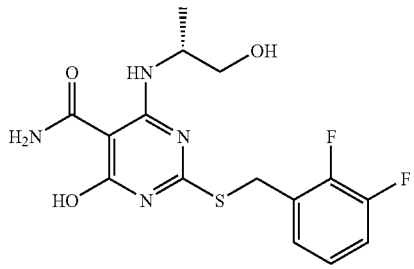

To the title product of Example 8 (0.230 g) was added ethanol (5 ml), water (5 ml) and potassium hydroxide (0.50 g). The reaction mixture was then heated at reflux for 16 h. To the reaction mixture was added more potassium hydroxide (1.0 g) at intervals and reaction reflux was continued for another 24 h. The reaction mixture was acidified with concentrated hydrochloric acid and extracted with EtOAc (2×50 ml). The combined organic layer was washed with water (2×20 ml), brine (10 ml) and dried (MgSO$_4$). The solid was filtered and the filtrate evaporated to dryness. The material was chromatographed on silica gel eluting with EtOAc to yield the title product as a white solid. Yield 5 mg.

MS APCI (+ve) 371 [M+H]$^+$ $^1$H NMR $\delta_{(DMSO)}$ 12.35 (1H, bs), 10.55 (1H, bs), 9.10 (1H, bs), 7.23-7.40 (2H, m) 7.14-7.22 (1H, m), 7.01 (1H, m), 4.86 (1H, t), 4.40-4.50 (2H, dd), 4.15-4.25 (1H, m), 3.30-3.45 (2H, m), 1.08 (3H, d).

Example 28

2-[(2,3-difluorobenzyl)thio]-6-{[(1R)-2-hydroxy-1-methylethyl]amino}-5-(5-methyl-1,2,4-oxadiazol-3-yl)pyrimidin-4-ol

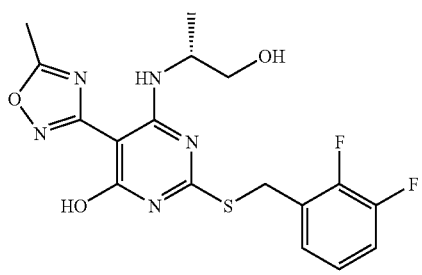

To the title product of Example 8 step vi) (0.25 g) added ethanol (5 ml), hydroxylamine hydrochloride (0.11 g) and sodium ethoxide (0.1 g). The reaction mixture was stirred at room temperature for 2 h then heated at reflux for 16 h. The solvent was evaporated and to the residue were added toluene (10 ml), acetic anhydride (50 mg) and triethylamine (0.10 g). This mixture was heated at reflux for 2 h. The solvent was evaporated and the residue taken in methanol (20 ml) and aqueous 1M hydrochloric acid (10 ml). This was stirred for 30 min before the solvent was evaporated. The residue was extracted with EtOAc (2×50 ml). The organic layer was washed with water (2×20 ml), brine (10 ml) and dried (MgSO$_4$). The solid was filtered and the filtrate evaporated to dryness. The material was purified by reverse phase HPLC (95-25% 0.02M ammonium hydroxide/acetonitrile) to yield the title product as a white solid. Yield 4 mg.

MS APCI (+ve) 410 [M+H]$^+$ $^1$H NMR $\delta_{(CD_3OD)}$ 7.20-7.30 (1H, m) 6.99-7.08 (2H, m), 4.32-4.48 (2H+1H, m), 3.4-3.58 (2H, m), 2.51-2.55 (3H, bs), 1.12 (3H, d).

Example 29

2-[(2,3-difluorobenzyl)thio]-6-{[(1R)-2-hydroxy-1-methylethyl]amino}-5-(1,3-oxazol-5-yl)pyrimidin-4-ol

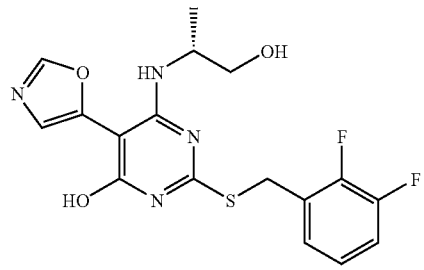

To the subtitle product of Example 29 step iii) (0.48 g) was added methanol (10 ml), p-toluenesulfonylmethyl isocyanide (0.18 g) and potassium carbonate (0.13 g). The reaction mixture was heated at reflux for 2 h. The solvent was evaporated and the residue treated with hydrochloric acid (1M, 10 ml) and methanol (30 ml). The reaction was stirred at room temperature for 10 min. The solvent was evaporated and the residue extracted with EtOAc (2×50 ml), washed with saturated sodium carbonate (10 ml), brine (20 ml) and dried (MgSO$_4$). The solvent was evaporated and the residue, diluted in DCM (10 ml), treated with diethylamine (0.50 g) and tetrakis(triphenylphosphine)palladium (79 mg). The reaction was stirred at room temperature for 1 h before the solvent was evaporated and the residue suspended in aqueous hydrochloric acid (50 ml) and extracted with EtOAc (2×50 ml). The organic layer was washed with brine (20 ml) and dried (MgSO$_4$). The solid was filtered and the filtrate evaporated to dryness to give a blue semi-solid. The residue was further purified by reverse phase HPLC with gradient elution in acetonitrile/0.02M ammonium hydroxide (95% to 25% aqueous phase, Ex-Terra) to yield the title product as a white solid. Yield 6 mg.

MS APCI (+ve) 395 [M+H]$^+$ $^1$H NMR $\delta_{(CD_3OD)}$ 8.30 (1H, s), 7.58 (1H, s), 7.30-7.41 (1H, m), 7.09-7.30 (2H, m) 4.40-4.70 (2H+1H, m), 3.7-3.85 (2H, m), 3.61-3.64 (1H, m), 1.21 (3H, d).

The intermediates for the above compound were prepared as follows:

i) 4-chloro-2-[(2,3-difluorobenzyl)thio]-6-{[(1R)-2-hydroxy-1-methylethyl]-amino}-pyrimidine-5-carbaldehyde A solution of (R)-alaninol (1.12 g) in DMF was added dropwise to the subtitle product of Example 8 step ii) (5.0 g) and triethylamine (2.1 ml) at −5° C. The mixture was allowed to come to room temperature and stirred for 1 h. To the mixture was added water (100 ml), the organics extracted with EtOAc (2×250 ml), the organic layers combined, washed with water (3×50 ml), brine (2×50 ml) and dried (MgSO$_4$). The solid was filtered and the filtrate evaporated to dryness to give the subtitle compound as a yellow solid. Yield 6.40 g.

MS APCI (+ve) 374 [M+H]$^+$ ii) 4-[((1R)-2-{[tert-butyl(dimethyl)silyl]oxy}-1-methylethyl)amino]-6-chloro-2-[(2,3-difluorobenzyl)thio]pyrimidine-5-carbaldehyde To a solution of the subtitle product of step i) (5.60 g) in DMF was added tert-butyldimethylsilyl chloride (2.40 g) at −10° C. in portions. To this mixture was then added imidazole in portions. The mixture was then stirred at 0° C. for 2 h before being quenched with excess water. The mixture was then extracted with EtOAc (2×250 ml), the combined organics washed with water (3×300 ml) and brine (2×30 ml). The organic layer was dried (MgSO$_4$) and solid was filtered. The filtrate was evaporated to dryness. The residue was purified by column chromatography (10% EtOAc/isohexane) to yield the subtitle compound as a white solid.

Yield 5.57 g.

MS APCI (+ve) 489 [M+H]$^+$ $^1$H NMR $\delta_{(CDCl_3)}$ 7.20-7.25 (1H, m), 6.97-7.10 (2H, m), 4.40 (3H, m), 3.61-3.63 (2H, m), 1.21 (3H, d), 0.91 (9H, s), 0.05 (6H, s).

iii) 4-(allyloxy)-6-[((1R)-2-{[tert-butyl(dimethyl)silyl]oxy}-1-methylethyl)amino]-2-[(2,3-difluorobenzyl)thio]pyrimidine-5-carbaldehyde To the subtitle product of step ii) (1.0 g) in toluene was added allyl alcohol (0.23 g), sodium hydroxide (0.16 g) and benzyltriethylammonium chloride (10 mg). The mixture was stirred at room temperature for 2 h before sodium hydroxide solution (10 ml, 1M) was added the organics extracted with EtOAc (2×50 ml). The combined organics were washed with brine (20 ml) and dried (MgSO$_4$). The solid was filtered and the filtrate evaporated to dryness to yield the subtitle compound as a white solid. Yield 1.0 g MS APCI (+ve) 510 [M+H]$^+$ $^1$HNMR $\delta_{(CDCl_3)}$ 10.14 (1H, s), 9.30 (1H, d), 7.20-7.25 (1H, m), 6.96-7.15 (2H, m), 5.96-6.08 (1H, m), 5.33-5.36 (1H, m), 5.24-5.28 (1H, m), 4.85-4.95 (2H, m) 4.38-4.40 (3H, m), 3.60-3.62 (2H, m), 1.21 (3H, d), 0.87 (9H, s), 0.01 (6H, s).

Example 30

2-[(2,3-difluorobenzyl)thio]-4-{[(1R)-1,2-dihydroxyethyl]amino}-6-hydroxy-N,N-dimethylpyrimidine-5-carboxamide

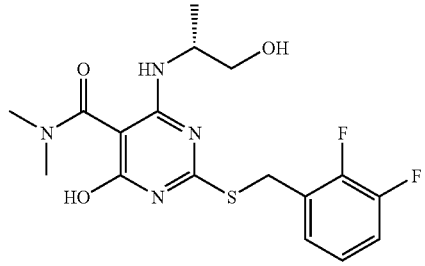

To the subtitle product of Example 30 step vii) (0.20 g) in toluene (2 ml) was added water (13 mg) and potassium tert-butoxide (84 mg). The mixture was then heated at reflux for 3 h before more water (20 mg) and potassium tert-butoxide (84 mg) were added and heating maintained for another 1 h. The solvent was evaporated and the residue diluted in methanol (20 ml) and aqueous hydrochloric acid (5 ml). When the reaction was complete the volatiles were removed in vacuo and residue diluted in EtOAc (100 ml) and aqueous hydrochloric acid (20 ml). The organic layer was washed with water (20 ml), brine (20 ml) and dried (MgSO$_4$). The solid was filtered and the filtrate evaporated to dryness to give the crude product. This residue was purified by reverse phase HPLC with gradient elution in acetonitrile/0.02M ammonium hydroxide (95% to 25% aqueous phase, Ex-Terra) to yield the title product as a white solid. Yield 15 mg.

MS APCI (+ve) 399 [M+H]$^+$ $^1$H NMR $\delta_{(DMSO)}$ 7.23-7.33 (2H, m) 7.13-7.19 (1H, m), 6.81 (1H, m), 4.40-4.58 (2H, m), 4.05-4.21 (1H, m), 3.30-3.45 (2H, m), 2.80 (6H, 2s), 1.25 (3H, d).

The intermediates for the above compound were prepared as follows:

i) 2,4,6-trichloropyrimidine-5-carbaldehyde

To phosphorus oxychloride (329 g) at 0° C. was added DMF (44.5 g) dropwise to give a slurry. This was stirred at 20° C. for 2 h and pyrimidine-2,4,6-triol (30 g) added in portions. The mixture was stirred at room temperature for 2 h and then heated at 100° C. for 12 h. The phosphorus oxychloride was removed in vacuo and the residue poured onto ice. The resulting solid was filtered and washed with water (100 ml). The solid was extracted with EtOAc (3×200 ml). The combined organics were washed with water (200 ml), brine (100 ml) and dried (MgSO$_4$). The solid was filtered and the solvent evaporated to afford the subtitle compound as a yellow oil. Yield 20.0 g.

GC-MS 209 [M$^+$].

ii) 2,4,6-trichloropyrimidine-5-carbonyl chloride

To the subtitle product of step i) (5.0 g) in dichloroethane (25 ml) was added aza-bis-isobutyronitrile (25 mg) and the mixture heated to 60° C. Sulfuryl chloride (3.67 g) was then added and the reaction heated at 75° C. for 4 h. The same amount of aza-bis-isobutyronitrile (4×25 mg) and sulfuryl chloride (4×3.36 g) was added for 4 days on each day interval. The solvent was evaporated to give a yellow oil which was distilled under reduced pressure to yield the subtitle compound as a yellow oil. Yield 5.8 g.

GC-MS 245 [M$^+$].

iii) 2,4,6-trichloro-N,N-dimethylpyrimidine-5-carboxamide

To a solution of the subtitle product of step ii) (2.0 g) in DCM (20 ml) and sodium bicarbonate (1.36 g) in water (20 ml) at 0° C. was added dimethylamine (1.00 ml, 40% aqueous) dropwise. The reaction mixture was stirred at room temperature for 2 h before DCM (40 ml) was added and the aqueous layer separated. The organic layer was washed with water (20 ml), brine (10 ml) and dried (MgSO$_4$). The solid was filtered and the solvent evaporated to dryness under reduced pressure. The residue was purified by column chromatography (EtOAc/isohexane (1:1)) to yield the subtitle compound as an off white solid. Yield 1.9 g MS APCI (+ve) 255 [M+H]$^+$ $^1$H NMR $\delta_{(CDCl_3)}$ 3.18 (3H, s), 2.96 (3H, s).

iv) 2,4-dichloro-6-{[(1R)-1,2-dihydroxyethyl]amino}-N,N-dimethylpyrimidine-5-carboxamide (R)-alaninol (0.46 g) in DMF (20 ml) was added dropwise to the subtitle product of step iii) (1.60 g) at −5° C. To this mixture was added triethylamine (0.63 g), the mixture allowed to come to room temperature and stirred for 1 h. To the mixture was added water (60 ml) and EtOAc (2×200 ml). The organic layer was washed With water (3×50 ml), brine (30 ml) and dried (MgSO$_4$). The solid was filtered and the filtrate evaporated to dryness to give a yellow solid. This was chromatographed using EtOAc as eluent to yield the subtitle compound.

Yield 1.07 g

MS APCI (+ve) 294 [M+H]$^+$ $^1$H NMR $\delta_{(CDCl_3)}$ 5.90-5.97 (1H, m), 4.31-4.40 (1H, m), 3.73-3.77 (1H, m), 3.57-3.73 (1H, m), 3.13 (3H, s), 3.03 (3H, s), 1.26 (3H, d).

v) 4[((1R)-2-{[tert-butyl(dimethyl)silyl]oxy}-1-hydroxyethyl)amino]-2,6-dichloro-N,N-dimethylpyrimidine-5-carboxamide To a solution of the subtitle product of step iv) (0.50 g) in DMF (10 ml) was added tert-butyldimethylsilyl chloride (0.51 g) at −10° C. in portions. To this mixture was then added imidazole in portions. The mixture was then stirred at 0° C. for 1 h and allowed to come to room temperature and stirred for 16 h. The mixture was quenched with water and extracted with EtOAc (2×250 ml). The combined organics were washed with water (3×20 ml) and brine (3×20 ml), the organic layer dried (MgSO$_4$) and the solid filtered. The filtrate was evaporated to dryness and the residue chromatographed on silica gel eluting with EtOAc/isohexane (1:1) to yield the subtitle compound as an oil. Yield 1.0 g.

MS APCI (+ve) 407 [M+H]$^+$ $^1$H NMR $\delta_{CDCl_3}$ 6.00 (1/2H, d), 5.90 (1/2H, d), 4.20-4.40 (1H, m), 3.50-3.61 (2H, m), 3.10 (3H, s), 2.97 (3H, s), 1.22-1.28 (3H, m), 0.89-0.90 (9H, d), 0.01-0.06 (6H, m).

vi) (3,4-difluorophenyl)methanethiol

Thiourea (5.0 g) was added to a solution of 3,4-difluorobenzyl bromide (13.6 g) in ethanol (100 ml). The mixture was heated at reflux for 3 h before removal of the volatiles in vacuo. The crude solid was suspended in aqueous sodium hydroxide solution (1.6M, 110 ml) and heated at reflux for 3 h before allowing to cool to room temperature. The reaction was acidified with concentrated hydrochloric acid and the organics extracted with ether (200 ml). The organic layer was washed with saturated sodium bicarbonate solution (2×50 ml), brine (20 ml), dried (MgSO$_4$), and concentrated in vacuo to provide the subtitle product as a colourless oil. Yield 11.1 g $^1$H NMR $\delta_{(CDCl_3)}$ 7.00-7.11 (3H, m), 3.78 (2H, d), and 1.90 (1H, t)

vii) 4-[((1R)-2-{[tert-butyl(dimethyl)silyl]oxy}-1-hydroxyethyl)amino]-6-chloro-2-[(2,3-difluorobenzyl)thio]-N,N-dimethylpyrimidine-5-carboxamide To the subtitle product of step v) (0.9 g) in methanol (10 ml) was added the subtitle product of step vi) (0.35 g) and triethylamine (0.22 g) at 0° C. The mixture was allowed to come to room temperature and stirred there for 2 days. To the reaction mixture was added more 3,4-difluorobenzyl thiol (35 mg) and triethylamine (22 mg). and stirred for 24 h. The solvent was evaporated and the residue purified by column chromatography (EtOAc/isohexane (1:1)) to give the subtitle compound as a solid. Yield 0.45 g MS APCI (+ve) 532 [M+H]$^+$ $^1$H NMR $\delta_{(CDCl_3)}$ 7.25 (1H, m), 6.95-7.10 (2H, m), 5.81 (1/2H, d), 5.70 (1/2H, d), 4.30-4.40 (2H, dd), 4.15-4.30 (1H, m), 3.50-3.61 (2H, m), 3.10 (3H, s), 2.97 (3H, s), 1.10-1.20 (3H, m), 0.92 (9H, d), 0.01-0.06 (6H, m).

Example 31

2-[(2,3-difluorobenzyl)thio]-5-fluoro-6-{[(1R)-2-hydroxy-1-methylethyl]amino}-pyrimidin-4-ol

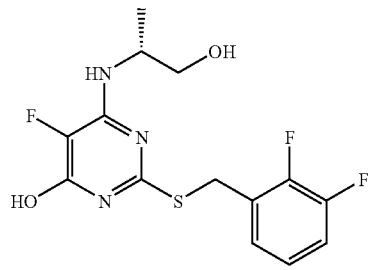

To the subtitle product from Example 9 step i) (0.85 g) in methanol (20 ml) was added Selectfluor™ (1.01 g). The mixture was stirred at room temperature for 5 days before the solids were filtered and the solvent removed under reduced pressure. The residue was diluted in EtOAc (10 ml) and hydrochloric acid (1M, 20 ml) added and stirred at room temperature for 1 h. EtOAc (50 ml) was added and the organic layer was separated and washed with aqueous hydrochloric acid (2×20 ml), brine (20 ml) and dried (MgSO$_4$). The solid was filtered and the solvent evaporated to dryness to give yellow solid which was chromatographed eluting with EtOAc to 2% methanol/EtOAc to yield the subtitle compound as a white solid. Yield 0.12 g.

MS APCI (+ve) 346 [M+H]$^+$ $^1$H NMR $\delta_{(DMSO)}$ 7.31-7.37 (2H, m) 7.13-7.19 (1H, m), 6.68 (1H, br. s), 4.69 (1H, t), 4.39-4.50 (2H, m), 4.08-4.15 (1H, m), 3.31-3.39 (1H, m), 2.29-3.39 (1H, m), 1.07 (3H, d).

Example 32

2-[(3,4-difluorobenzyl)thio]-5-fluoro-6-{[(1R)-2-hydroxy-1-methylethyl]amino}-pyrimidin-4-ol

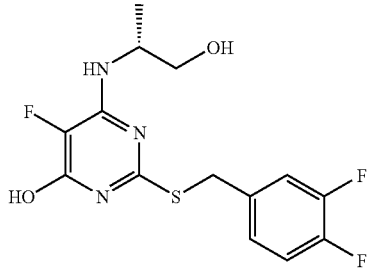

To the subtitle product of step i) (0.38 g) in methanol (10 ml) was added Selectfluor™ (0.45 g). The mixture was stirred at room temperature for 2 days before the solvent was removed under reduced pressure and the residue stripped with methanol (3×100 ml). The residue was diluted in EtOAc (100 ml) and washed with aqueous hydrochloric acid (1M, 20 ml), water (2×20 ml), brine (20 ml) and dried (MgSO$_4$). The solid was filtered and solvent evaporated to dryness to give a yellow solid which was chromatographed eluting with EtOAc to 2% methanol/EtOAc to yield the title compound as a white solid. Yield 25 mg.

MS APCI (+ve) 346 [M+H]$^+$ $^1$H NMR δ$_{(DMSO)}$ 7.45-7.50 (1H, m), 7.35-7.40 (1H, m) 7.27-7.33 (1H, m), 6.65 (1H, br. s), 4.69 (1H, t), 4.29-4.36 (2H, m), 4.08-4.15 (1H, m), 3.40-3.45 (1H, m), 3.32-3.33 (1H, m), 1.07 (3H, d).

Intermediates for this compound were prepared as follows:

i) 2-[(3,4-difluorobenzyl)thio]-6-{[(1R)-2-hydroxy-1-methylethyl]amino}pyrimidin-4-ol To the subtitle product of Example 1 step i) (5.45 g) was added ethanol (100 ml) and sodium hydroxide (1.30 g, 33 ml) and stirred for 10 min before adding 3,4-difluorobenzyl bromide (6.70 g) and stirring for 16 h. The solvent was evaporated and the residue diluted in EtOAc (2×200 ml) and acidified with aqueous hydrochloric acid until pH<4. The organic layer was washed with brine (40 ml) and dried (MgSO$_4$). The solid was filtered and the filtrate evaporated to dryness. The residue was purified by silica gel chromatography eluting with EtOAc/methanol (5%) to afford the subtitle product as an oil. Yield 0.38 g MS APCI (+ve) 328 [M+H]$^+$ $^1$H NMR δ$_{(DMSO)}$ 7.48-7.53 (1H, m), 7.30-7.40 (1H, m) 7.27-7.30 (1H, m), 6.77 (1H, br. s), 4.98 (1H, br. s), 4.71 (1H, t), 4.31 (2H, s), 3.40-3.45 (1H, m), 3.25-3.29 (1H, m), 1.07 (3H, d).

Example 33

2-[(3-fluorobenzyl)thio]-5-fluoro-6-{[(1R)-2-hydroxy-1-methylethyl]amino}pyrimidin-4-ol

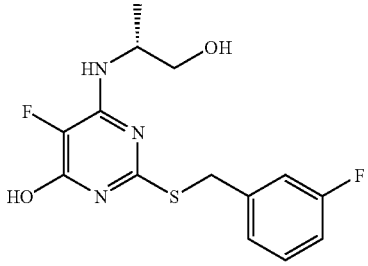

To the subtitle product of step i) in methanol (20 ml) was added Selectfluor™ (0.69 g). The mixture was stirred at room temperature for 5 days. The solvent was filtered and the filtrate evaporated to dryness and the residue chromatographed eluting with EtOAc to 5% methanol/EtOAc to yield the title compound as a white solid. Yield 35 mg.

MS APCI (+ve) 328 [M+H]$^+$ $^1$H NMR δ$_{(DMSO)}$ 7.31-7.37 (1H, m) 7.23-7.26 (2H, m), 7.05-7.10 (1H, m), 6.65 (1H, br. s), 4.69 (1H, t), 4.31-4.40 (2H, m), 4.08-4.15 (1H, m), 3.40-3.50 (1H, m), 3.36-3.40 (1H, m), 1.07 (3H, d).

Intermediates for this compound were prepared as follows:

i) 2-[(3-fluorobenzyl)thio]-6-{[(1R)-2-hydroxy-1-methylethyl]amino}pyrimidin-4-ol To the subtitle product of Example 1 step i) (3.12 g) was added ethanol (100 ml) and sodium hydroxide (20 ml, 1M) and stirred for 10 min. To this mixture was added 3-fluorobenzyl bromide (2.83 g) and stirred for 16 h. The solvent was evaporated and the residue diluted in EtOAc (2×200 ml) and acidified with aqueous hydrochloric acid until pH<4. The organic layer was washed with brine (40 ml) and dried (MgSO$_4$). The solid was filtered and the filtrate evaporated to dryness. The residue was purified by silica gel chromatography eluting with EtOAc/methanol (5%) to afford the subtitle product as a yellow oil. Yield 0.50 g MS APCI (+ve) 310 [M+H]$^+$ $^1$H NMR δ$_{(DMSO)}$ 7.32-7.40 (1H, m) 7.25-7.27 (2H, m), 7.04-7.09 (1H, m), 6.77 (1H, br. s), 4.71 (1H, t), 4.30-4.40 (2H, m), 3.20-3.45 (2H, m), 1.07 (3H, d).

Example 34

2-[(4-fluorobenzyl)thio]-5-fluoro-6-{[(1R)-2-hydroxy-1-methylethyl]amino}pyrimidin-4-ol

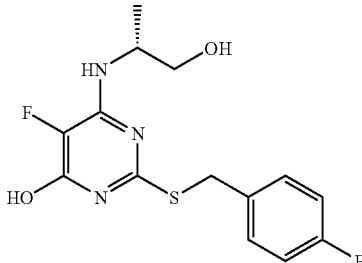

To the subtitle product of step i) (0.55 g) in methanol (10 ml) was added Selectfluor™ (0.25 g). The mixture was stirred at room temperature for 3 days. The solvent was filtered and the filtrate evaporated to dryness. The resulting material was chromatographed eluting with 5% methanol/EtOAc to yield the title compound as a white solid. Yield 15 mg.

MS APCI (+ve) 328 [M+H]+

$^1$H NMR $\delta_{(DMSO)}$ 7.42-7.46 (2H, m) 7.10-7.20 (2H, m), 6.65 (1H, br. s), 4.69 (1H, t), 4.31-4.40 (2H, m), 4.10-4.20 (1H, m), 3.40-3.50 (1H, m), 3.30-3.40 (1H, m), 1.07 (3H, d).

The intermediate for this compound was prepared as follows.

i) 2-[(4-fluorobenzyl)thio]-6-{[(1R)-2-hydroxy-1-methylethyl]amino}pyrimidin-4-ol To the subtitle product of Example 1 step i) (3.12 g) added ethanol (100 ml) and sodium hydroxide (0.68 g) and stirred for 10 min. To this mixture was added 4-fluorobenzyl bromide (2.83 g) and stirred for 16 h. The solvent was evaporated and the residue diluted in EtOAc (2×200 ml) and acidified with aqueous hydrochloric acid until pH<4. The organic layer was washed with brine (40 ml) and dried (MgSO$_4$). The solid was filtered and the filtrate evaporated to dryness. The residue was chromatographed over silica gel eluting with 5% methanol/EtOAc to afford the subtitle product as a yellow oil. Yield 0.20 g MS APCI (+ve) 310 [M+H]+

$^1$H NMR $\delta_{(DMSO)}$ 7.43-7.47 (2H, m) 7.10-7.16 (2H, m), 6.77 (1H, br. s), 4.95 (1H, br. s), 4.71 (1H, t), 4.33 (2H, s), 3.24-3.45 (2H, m), 1.09 (3H, d).

The invention claimed is:

1. A compound of formula (1) or a pharmaceutically acceptable salt thereof:

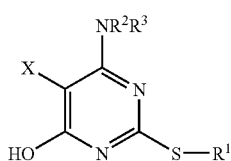

(1)

wherein R$^1$ is a group selected from C$_{3-7}$carbocyclyl, C$_{1-8}$alkyl, C$_{2-6}$alkenyl and C$_{2-6}$alkynyl; wherein the group is substituted by 1, 2 or 3 substituents independently selected from fluoro, nitrile, —OR$^4$, —NR$^5$R$^6$, —CONR$^5$R$^6$, —COOR$^7$, —NR$^8$COR$^9$, —SR$^{10}$, —SO$_2$R$^{10}$,
  —SO$_2$NR$^5$R$^6$, —NR$^8$SO$_2$R$^9$, phenyl or heteroaryl; wherein phenyl and heteroaryl are optionally substituted by 1, 2 or 3 substituents independently selected from halo, cyano, nitro, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$, C$_{1-6}$alkyl and trifluoromethyl;

wherein R$^2$ is C$_{3-7}$carbocyclyl, optionally substituted by 1, 2 or 3 substituents independently selected from:

(a) fluoro, —OR$^4$, —NR$^5$R$^6$—CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$;

(b) a 3-8 membered ring optionally containing 1, 2 or 3 atoms selected from O, S, —NR$^8$ and whereby the ring is optionally substituted by C$_{1-3}$alkyl or fluoro; or (c) phenyl or heteroaryl, each of which is optionally substituted by 1, 2 or 3 substituents independently selected from halo, cyano, nitro, —OR$^4$, —NR$^5$R$^6$, —CONR$^5$R$^6$, —NR$^8$COR$^9$, —SO$_2$NR$^5$R$^6$, —NR$^8$SO$_2$R$^9$, C$_{1-6}$alkyl and trifluoromethyl;

or R$^2$ is a group selected from C$_{1-8}$alkyl, C$_{2-6}$alkenyl or C$_{2-6}$alkynyl wherein the group is substituted by 1, 2 or 3 substituents independently selected from hydroxy, amino, C$_{1-6}$alkoxy, C$_{1-6}$alkylamino, di(C$_{1-6}$alkyl)amino, N—(C$_{1-6}$ alkyl)-N-(phenyl)amino, N—C$_{1-6}$ alkylcarbamoyl, N,N—(C$_{1-6}$alkyl)$_2$carbamoyl, N—(C$_{1-6}$ alkyl)-N-(phenyl)carbamoyl, carboxy, phenoxycarbonyl, —NR$^8$COR$^9$, —SO$_2$R$^{10}$, —SO$_2$NR$^5$R$^6$ and —NR$^8$SO$_2$R$^9$;

wherein R$^3$ is hydrogen or R$^2$;

R$^4$ is hydrogen or a group selected from C$_{1-6}$alkyl and phenyl, wherein the group is optionally substituted by 1 or 2 substituents independently selected from halo, phenyl, —OR$^{11}$ and —NR$^{12}$R$^{13}$;

R$^5$ and R$^6$ are independently hydrogen or a group selected from C$_{1-6}$alkyl and phenyl wherein the group is optionally substituted by 1, 2 or 3 substituents independently selected from halo, phenyl, —OR$^{14}$, —NR$^{15}$R$^{16}$, —CONR$^{15}$R$^{16}$, —NR$^{15}$COR$^{16}$, —SONR$^{15}$R$^{16}$ and NR$^{15}$SO$_2$R$^{16}$ or R$^5$ and R$^6$ together with the nitrogen atom to which they are attached form a 4- to 7-membered saturated heterocyclic ring system optionally containing a further heteroatom selected from oxygen and nitrogen atoms, which ring system may be optionally substituted by 1, 2 or 3 substituents independently selected from phenyl, —OR$^{14}$, —COOR$^{14}$, —NR$^{15}$R$^{16}$, —CONR$^{15}$R$^{16}$, —NR$^{15}$COR$^{16}$, —SONR$^{15}$R$^{16}$, NR$^{15}$SO$_2$R$^{16}$ or C$_{1-6}$alkyl, optionally substituted by 1 or 2 substituents independently selected from halo, —NR$^{15}$R$^{16}$ and —OR$^{17}$ groups;

R$^{10}$ is hydrogen or a group selected from C$_{1-6}$alkyl or phenyl, wherein the group is optionally substituted by 1, 2 or 3 substituents independently selected from halo, phenyl, —OR$^{17}$ and —NR$^{15}$R$^{16}$; and each of R$^7$, R$^8$, R$^9$, R$^{11}$, R$^{12}$, R$^{13}$, R$^{14}$, R$^{15}$, R$^{16}$, R$^{17}$ is independently hydrogen, C$_{1-6}$alkyl or phenyl;

X is hydrogen, halo, cyano, nitro, hydroxy, C$_{1-6}$alkoxy, optionally substituted by 1 or 2 substituents selected from halo, —OR$^{11}$ and —NR$^{12}$R$^{13}$, —NR$^5$R$^6$, —COOR$^7$, —CONR$^5$R$^6$, —NR$^8$COR$^9$, thio, thiocyano, thio C$_{1-6}$alkyl, optionally substituted by 1 or 2 substituents selected from halo, —OR$^{17}$, —COOR$^7$, —NR$^{15}$R$^{16}$, —CONR$^5$R$^6$, —SO$_2$R$^{10}$, —SO$_2$NR$^5$R$^6$—NR$^8$SO$_2$R$^{10}$ or a group selected from C$_{3-7}$carbocyclyl, C$_{1-8}$alkyl, C$_{2-6}$alkenyl or C$_{2-6}$alkynyl, wherein the group is optionally substituted by 1, 2 or 3 substituents independently selected from halo, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$ and —NR$^8$SO$_2$R$^9$; or a -phenyl, -heteroaryl, -thiophenyl, -thioheteroaryl, aminoheteroaryl, and thio C$_{1-6}$alkylheteroaryl group, all of which may be optionally substituted by 1, 2 or 3 substituents independently selected from halo, cyano, nitro, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$, C$_1$-C$_6$alkyl, phenyl, heteroaryl or trifluoromethyl groups.

2. A compound according to claim 1 or a pharmaceutically acceptable salt thereof, wherein R$^1$ is C$_{1-8}$alkyl substituted by 1, 2 or 3 substituents independently selected from phenyl or heteroaryl, wherein phenyl and heteroaryl are optionally substituted by 1, 2 or 3 substituents independently selected from halo, cyano, —OR$^4$, —SR$^{10}$, C$_{1-6}$alkyl and trifluoromethyl.

3. A compound according to claim 1 or a pharmaceutically acceptable salt thereof, wherein R$^2$ is C$_{1-8}$alkyl substituted by 1, 2 or 3 substituents independently selected from hydroxy, amino, C$_{1-6}$alkoxy, C$_{1-6}$alkylamino, di(C$_{1-6}$alkyl)amino, N—(C$_{1-6}$alkyl)-N-phenyl)amino, N—C$_{1-4}$alkylcarbamoyl, N,N-di(C$_{1-6}$alkyl)carbamoyl, N—(C$_{1-6}$alkyl)-N-(phenyl)carbamoyl, carboxy, phenoxycarbonyl, —NR$^8$COR$^9$, —SO$_2$R$^{10}$, —SO$_2$NR$^5$R$^6$ and —NR$^8$SO$_2$R$^9$; and wherein R$^3$ is hydrogen.

4. A compound according to claim 1 or a pharmaceutically acceptable salt thereof, wherein R$^4$, R$^5$, R$^6$, R$^8$, R$^9$ and R$^{10}$ are independently hydrogen, C$_{1-4}$alkyl or phenyl.

5. A compound according to claim 1 or a pharmaceutically acceptable salt thereof, wherein X is hydrogen, halo, cyano, nitro, hydroxy, thio, thiocyano, —CONR$^5$R$^6$, thio C$_{1-6}$alkyl, optionally substituted by 1 or 2 substituents selected from halo, —OR$^{17}$, —NR$^{15}$R$^{16}$, —CONR$^5$R$^6$, —NR$^8$SO$_2$R$^{10}$, C$_{1-8}$alkyl, optionally substituted by 1, 2 or 3 substituents independently selected from halo, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$ and —NR$^8$SO$_2$R$^9$, heteroaryl, thioheteroaryl or thio C$_{1-4}$alkylheteroaryl all of which may be optionally substituted by 1, 2 or 3 substituents independently selected from halo, cyano, nitro, —OR$^4$, —NR$^5$R$^6$, —CONR$^5$R$^6$, —COOR$^7$, NR$^8$COR$^9$, —SR$^{10}$, —SO$_2$R$^{10}$, —SO$_2$NR$^5$R$^6$, —NR$^8$SO$_2$R$^9$, C$_{1-6}$alkyl, or trifluoromethyl.

6. A compound according to claim 2 or a pharmaceutically acceptable salt thereof, wherein R$^1$ is benzyl substituted by 1 or 2 substituents independently selected from fluoro, chloro, bromo, methoxy, methyl, and trifluoromethyl.

7. A compound according to claim 3 or a pharmaceutically acceptable salt thereof, wherein R$^2$ is C$_{1-4}$alkyl, substituted by 1, 2 or 3 substituents independently selected from hydroxy, amino, C$_{1-6}$alkoxy, C$_{1-6}$alkylamino, and di(C$_{1-6}$alkyl)amino; and R$^3$ is hydrogen.

8. A compound according to claim 4 or a pharmaceutically acceptable salt thereof, wherein X is hydrogen, fluoro, chloro, bromo, thiocyano, —NR$^8$SO$_2$R$^9$, where R$^8$ is hydrogen and R$^9$ is methyl, -thioimidazolyl, -thiotriazolyl, —CONH$_2$, —CONMe$_2$ or cyano.

9. A compound selected from the group consisting of:
2-(Benzylthio)-6-{[(1R)-2-hydroxy-1-methylethyl]amino}-4-pyrimidinol,
2-(Benzylthio)-5-chloro-6-{[(1R)-2-hydroxy-1-methylethyl]amino}-4-pyrimidinol,
2-[(3-Chlorobenzyl)thio]-6-{[(1R)-2-hydroxy-1-methylethyl]amino}-4-pyrimidinol,
5-Chloro-2-[(3-chlorobenzyl)thio]-6-{[(1R)-2-hydroxy-1-methylethyl]amino}-4-pyrimidinol,
2-[(3-Chlorobenzyl)thio]-4-hydroxy-6-{[(1R)-2-hydroxy-1-methylethyl]amino}-5-pyrimidinyl thiocyanate,
N-(2-[(3-Chlorobenzyl)thio]-4-hydroxy-6-{[(1R)-2-hydroxy-1-methylethyl]amino}-5-pyrimidinyl)methanesulfonamide,
2-[(3-Chlorobenzyl)thio]-5-fluoro-6-{[(1R)-2-hydroxy-1-methylethyl]amino}-4-pyrimidinol, 2-[(2,3-difluorobenzyl)thio]-4-hydroxy-6{[(1S)-2-hydroxy-1-methylethyl]amino}pyrimidine-5-carbonitrile,
5-Chloro-2-[[(2,3-difluorophenyl)methyl]thio]-6-[[(1R)-2-hydroxy-1-methylethyl]amino]-4-pyrimidinol,
2-[[(2,3-Difluorophenyl)methyl]thio]-6-[[(1R)-2-hydroxy-1-methylethyl]amino]-5-iodo-4-pyrimidinol,
2-[[(2,3-Difluorophenyl)methyl]thio]-6-[[(1R)-2-hydroxy-1-methylethyl]amino]-5-nitro-4-pyrimidinol,
2-[[(3-Chlorophenyl)methyl]thio]-6-[[(1R)-2-hydroxy-1-methylethyl]amino]-5-(1,3,4-thiadiazol-2-ylthio)-4-pyrimidinol,
2-[[(2,3-Difluorophenyl)methyl]thio]-6-[[(1R)-2-hydroxy-1-methylethyl]amino]-5-(1H-imidazol-2-ylthio)-4-pyrmidinol,
2-[[(2,3-Difluorophenyl)methyl]thio]-5-[[2-(dimethylamino)ethyl]thio]-6-[[(1R)-2-hydroxy-1-methylethyl]amino]-4-pyrimidinol,
1-[2-[[(2,3-Difluorophenyl)methyl]thio]-4-hydroxy-6-[[(1R)-2-hydroxy-1-methylethyl]amino]-5-pyrimidinyl]-4(1H)-pyridinethione,
2-[[(2,3-Difluorophenyl)methyl]thio]-6-[[(1R)-2-hydroxy-1-methylethyl]amino]-5-(4-pyridinylthio)-4-pyrimidinol,
2-[[(2,3-Difluorophenyl)methyl]thio]-6-[[(1R)-2-hydroxy-1-methylethyl]amino]-5-(1H-1,2,4-triazol-3-ylthio)-4-pyrimidinol,
2-[[(2,3-Difluorophenyl)methyl]thio]-6-[[(1R)-2-hydroxy-1-methylethyl]amino]-5-[(4-methyl-4H-1,2,4-triazol-3-yl)thio]-4-pyrimidinol,
5-[(5-Amino-4H-1,2,4-triazol-3-yl)thio]-2-[[(2,3-difluorophenyl)methyl]thio]-6-[[(1R)-2-hydroxy-1-methylethyl]amino]-4-pyrimidinol,
2-[[(2,3-Difluorophenyl)methyl]thio]-6-[[(1R)-2-hydroxy-1-methylethyl]amino]-5-[[5-(4-pyridinyl)-1,3,4-oxadiazol-2-yl]thio]-4-pyrimidinol,
Ethyl[[2-[[(2,3-difluorophenyl)methyl]thio]-4-hydroxy-6-[[(1R)-2-hydroxy-1-methylethyl]amino]-5-pyrimidinyl]thio]-AcOH,
2-[[2-[[(2,3-Difluorophenyl)methyl]thio]-4-hydroxy-6-[[(1R)-2-hydroxy-1-methylethyl]amino]-5-pyrimidinyl]thio]-N-methyl-acetamide,
2-[[2-[[(2,3-Difluorophenyl)methyl]thio]-4-hydroxy-6-[[(1R)-2-hydroxy-1-methylethyl]amino]-5-pyrimidinyl]thio]-N-[2-(dimethylamino)ethyl]-acetamide,
1-[[[2-[[(2,3-Difluorophenyl)methyl]thio]-4-hydroxy-6-[[(1R)-2-hydroxy-1-methylethyl]amino]-5-pyrimidinyl]thio]acetyl]-piperazine,
2-[[(2,3-Difluorophenyl)methyl]thio]-6-[[(1R)-2-hydroxy-1-methylethyl]amino]-5-[(4-methyl-2-oxazolyl)thio]-4-pyrimidinol,
2-[[(2,3-Difluorophenyl)methyl]thio]-6-[[(1R)-2-hydroxy-1-methylethyl]amino]-5-[(1,2,4-oxadiazol-3-ylmethyl)thio]-4-pyrimidinol,
2-[(2,3-difluorobenzyl)thio]-4-{[(1R)-1,2-dihydroxyethyl]amino}-6-hydroxypyrimidine-5-carboxamide, 2-[(2,3-difluorobenzyl)thio]-6-{[(1R)-2-hydroxy-1-methylethyl]amino}-5-(5-methyl-1,2,4-oxadiazol-3-yl)pyrimidin-4-ol, 2-[(2,3-difluorobenzyl)thio]-6-{[(1R)-2-hydroxy-1-methylethyl]amino}-5-(1,3-oxazol-5-yl)pyrimidin-4-ol, 2-[(2,3-difluorobenzyl)thio]-4-{[(1R)-1,2-dihydroxyethyl]amino}-6-hydroxy-N,N-dimethylpyrimidine-5-carboxamide, 2-[(2,3-difluorobenzyl)thio]-5-fluoro-6-{[(1R)-2-hydroxy-1-methylethyl]amino}-pyrimidin-4-ol, 2-[(3,4-difluorobenzyl)thio]-5-fluoro-6-{[(1R)-2-hydroxy-1-methylethyl]amino}-pyrimidin-4-ol, 2-[(3-fluorobenzyl)thio]-5-fluoro-6-{[(1R)-2-hydroxy-1-methylethyl]amino}pyrimidin-4-ol, or 2-[(4-fluorobenzyl)thio]-5-fluoro-6-{[(1R)-2-hydroxy-1-methylethyl]amino}pyrimidin-4-ol or a pharmaceutically acceptable salt thereof.

10. A pharmaceutical composition comprising a compound or a pharmaceutically acceptable salt thereof according to claim 1; and a pharmaceutically-acceptable diluent or carrier.

11. A pharmaceutical composition which comprises a compound of claim 1, formula (1) or a pharmaceutically acceptable salt thereof, in conjunction with another pharmaceutical agent.

* * * * *

UNITED STATES PATENT AND TRADEMARK OFFICE
CERTIFICATE OF CORRECTION

PATENT NO. : 7,482,355 B2  Page 1 of 1
APPLICATION NO. : 10/525495
DATED : January 27, 2009
INVENTOR(S) : Ebden et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 678 days.

Signed and Sealed this

Seventh Day of September, 2010

David J. Kappos
*Director of the United States Patent and Trademark Office*